United States Patent [19]
Celis et al.

[11] Patent Number: 5,846,827
[45] Date of Patent: Dec. 8, 1998

[54] METHODS FOR EX VIVO THERAPY USING PEPTIDE-LOADED ANTIGEN PRESENTING CELLS FOR THE ACTIVATION OF CTL

[75] Inventors: Esteban Celis; Ralph Kubo; Horacio Serra; Van Tsai; Peggy Wentworth, all of San Diego, Calif.

[73] Assignee: Cytel Corporation, San Diego, Calif.

[21] Appl. No.: 468,454
[22] Filed: Jun. 6, 1995

Related U.S. Application Data

[63] Continuation of Ser. No. 103,401, Aug. 6, 1993, abandoned.
[51] Int. Cl.$^6$ .............................. C12N 5/06; A61K 45/00
[52] U.S. Cl. ........................ 435/384; 435/325; 435/386; 424/93.1; 424/93.7; 424/93.71
[58] Field of Search .................................. 424/93.1, 93.7, 424/93.71; 435/240.1, 240.21, 325, 384, 386

[56] References Cited

U.S. PATENT DOCUMENTS 5,081,029   1/1992   Zarling et al. ........................ 435/172.3

OTHER PUBLICATIONS

Klimas et al., AIDS 8:1073–1081 (1994).
Riddell et al., Annu. Rev. Immunol. 13:545–586 (1995).
Hsueh et al., Cellular Immunology 159:271–279 (1994).
D. Torpey III et al. (1993) Clinical Immunology and Immunopathology 68(3):263–272.
Clerici, et al., "Detection of Cytotoxic T Lymphocytes Specific for Synthetic Peptides of gp160 in HIV–Seropositive Individuals," *J. Immunol.*, 146(7):2214–2219 (Apr. 1, 1991).
Koenig, et al., "Determination of epitopes recognized by HIV–specific TL," *Int. Conf. AIDS* (Canada) (4–9 Jun. 1989), 5:531, abstract No. W.C.O. 41 (1989).
Lee et al., Hematology/Oncology Clinics of North America 8(6):1203–1221 (1994).
Fox, Bio/Technology 12:128 (1994).
Epperson, D.E. et al., "Cytokines Increase Transporter in Antigen Processing–1 Expression More Rapidly than HLA Class I Expression in Endothelial Cells," *J. Immunology*, 149(10):3297–3301 (15 Nov. 1992).
Smith, J.D., et al., "Extensive peptide ligand exchange by surface class I major histocompatibility complex molecules independent of exogenous $\beta_2$–microglobulin," *Proc. Natl. Acad. Sci USA*, 89:7767–7771 (Aug. 1992).
Van Bleek, G.M., et al., "Isolation of an endogenously processed immunodominant viral peptide from the class I H–2K$^b$ molecule," *Nature*, 348:213–216 (15 Nov. 1990).
Greenberg, P.D., "Adoptive T Cell Therapy of Tumors: Mechanisms Operative in the Recognition and Elimination of Tumor Cells," *Advances in Immunology*, pp. 281–355 (Jun. 1990).
Riddell, S.R., et al., "Restoration of Viral Immunity in Immunodeficient Humans by the Adoptive Transfer of T Cell Clones," *Science*, 257:238–241 (10 Jul. 1992).
Kantor, J., et al., "Antitumor Activity and Immune Responses Induced by a Recombinant Carcinoembryonic Antigen–Vaccinia Virus Vaccine," *J. Nat'l. Cancer Institute*, 84(14):1084–1091 (15 Jul. 1992).
Ioannides, C.G., et al., "T–Cell Recognition of Oncogene Products: A New Strategy for Immunotherapy," *Molecular Carcinogenesis*, 6:77–82 (1992).
Rosenberg, S.A., "Immunotherapy of Cancer Using Interleukin 2: Current Status and Future Prospects," *Immunology Today*, 9(2):58–61 (1988).
Callard, R.E., et al., "CD19 Regulation of Human B Cell Responses," *J. Immunology*, 148(10):2983–2987 (15 May 1992).
Sakane, T., et al., "Protein A from *Staphylococcus aureus*—A Mitogen for Human T Lymphocytes and B Lymphocytes but not L Lymphocytes," *J. Immunology*, 120(1):302–311 (Jan. 1978).
Falkoff, R.J.M., et al., "Separate Signals for Human B Cell Proliferation and Differentiation in Response to *Staphylococcus aureus:* Evidence for a Two–Signal Model of B Cell Activation," *J. Immunology*, 129(1);97–102 (Jul. 1982).
Pryjma, J., et al., "Induction and Suppression of Immunoglobulin Synthesis in Cultures of Human Lymphocytes: Effects of Pokeweed Mitogen and *Staphylococcus aureus* Cowan I," *J. Immunology*, 124(2):656–661 (Feb. 1980).
Bjorkman, P.J., et al., "Structure of the human class I histocompatibility antigen, HLA–A2," *Nature*, 329:506–512 (8 Oct. 1987).
Bjorkman, P.J., et al., "The foreign antigen binding site and T cell recognition regions of class I histocompatibility antigens," *Nature*, 329:512–518 (8 Oct. 1987).
Falk, K., et al., "Allele–specific motifs revealed by sequencing of self–peptides eluted from MHC molecules," *Nature*, 351:290–296 (23 May 1991).
Lamb, J.R., et al, "T–Cell Recognition of Influenza Viral Antigens," *Human Immunology*, 19:79–89 (1987).
De Bruijn, M.L.H., et al., "Peptide loading of empty major histocompatibility complex molecules on RMA–S cells allows the induction of primary cytotoxic T lymphocyte responses," *Eur. J. Immunol.*, 21:2963–2970 (1991).
Parham, P., "Transporters of Delight," *Nature*, 348:674–675 (20/27 Dec. 1990).
Kos, F.J., et al., "Induction of primary anti–viral cytotoxic T cells by in vitro stimulation with short synthetic peptide and interleukin–7," *Eur. J. Immunol.*, 22:3183–3185 (1992).

(List continued on next page.)

*Primary Examiner*—George C. Elliott
*Assistant Examiner*—Johnny F. Railey, II
*Attorney, Agent, or Firm*—Townsend and Townsend Crew LLP

[57] ABSTRACT

Methods for activating cytotoxic T lymphocytes (CTL) in vitro are presented in conjunction with methods for using the activated CTL for therapy in vivo. Additionally, a method for killing specific CTL in vivo is presented using antigen presenting cells which were modified in vitro.

16 Claims, 11 Drawing Sheets

OTHER PUBLICATIONS

Alderson, M.R., et al., "Interleukin 7 Enhances Cytolytic T Lymphocyte Generation and Induces Lymphokine–activated Killer Cells from Human Peripheral Blood," *J. Exp. Med.*, 172:577–587 (Aug. 1990).

Guilhot, S., et al., "Hepatitis B Virus (HBV)–Specific Cytotoxic T–Cell Response in Humans: Production of Target Cells by Stable Expression of HBV–Encoded Proteins in Immortalized Human B–Cell Lines," *J. Virology*, 66(5):2670–2678 (May 1992).

Azuma, M., et al., "CD28 Interaction with B7 Costimulates Primary Allogeneic Proliferative responses and Cytotoxicity Mediated by Small, Resting T Lymphocytes," *J. Exp. Med.*, 175:353–360 (Feb. 1992).

Harding, F.A., et al., "CD28–mediated signalling co–stimulates murine T cells and prevents induction of anergy in T–cell clones," *Nature*, 356:607–609 (16 Apr. 1992).

Linsley, P.S., et al., "Binding of the B Cell Activation Antigen B7 to CD28 Costimulates T Cell Proliferation and Interleukin 2 mRNA Accumulation," *J. Exp. Med.*, 173:721–730 (Mar. 1991).

Schwartz, R.H., "A Cell Culture Model for T Lymphocyte Clonal Anergy," *Science*, 248:1349–1356 (15 Jun. 1990).

Zhou, X., et al., "In vivo primary induction of virus–specific CTL by immunization with 9–mer synthetic peptides," *J. Immunological Methods*, 153:193–200 (1992).

Nikolic–Zugic, J., et al., "Peptide Presentation by Class–I Major Histocompatibility Complex Molecules," *Immunol. Res.*, 10:54–65 (1991).

Madden, D.R., et al., "The structure of HLA–B27 reveals nonamer self–peptides bound in an extended conformation," *Nature*, 353:321–324 (26 Sep. 1991).

Kubitscheck, U., et al., "Peptide Binding to Class I Molecules of the Major Histocompatibility Complex on the Surface of Living Target Cells," *Scand J. Immunol.*, 36:341–348 (1992).

Sugawara, S., et al., "A simple method to eliminate the antigenicity of surface class I MHC molecules from the membrane of viable cells by acid treatment at pH 3," *J. Immunological Methods*, 100:83–90 (1987).

Rotzschke, O., et al., "Naturally–occurring peptide antigens derived from the MHC class–I–restricted processing pathway," *Immunology Today*, 12(1):447–453 (1991).

Sette, A., et al., "Peptide Binding to HLA Class I Molecules Measured by a Quantitative Molecular Binding Assay," *Cell*, 74:1–9 (10 Sep. 1993).

Mamula, M.J., et al., "Do B cells drive the diversification of immune responses?" *Immunology Today*, 14(4):151–152 (1993).

Saiki, O., et al., "Synergistic Effects of Human B and T Lymphocyte Mitogens Induce Uniform, High Levels of Immunoglobulin Secretion Among Normal Donors," *J. Immunological Methods*, 45:221–226 (1981).

Hoffenbach, A., et al., "Unusually High Frequencies of HIV–Specific Cytotoxic T Lymphocytes in Humans," *J. Immunology*, 142(2):452–462 (15 Jan. 1989).

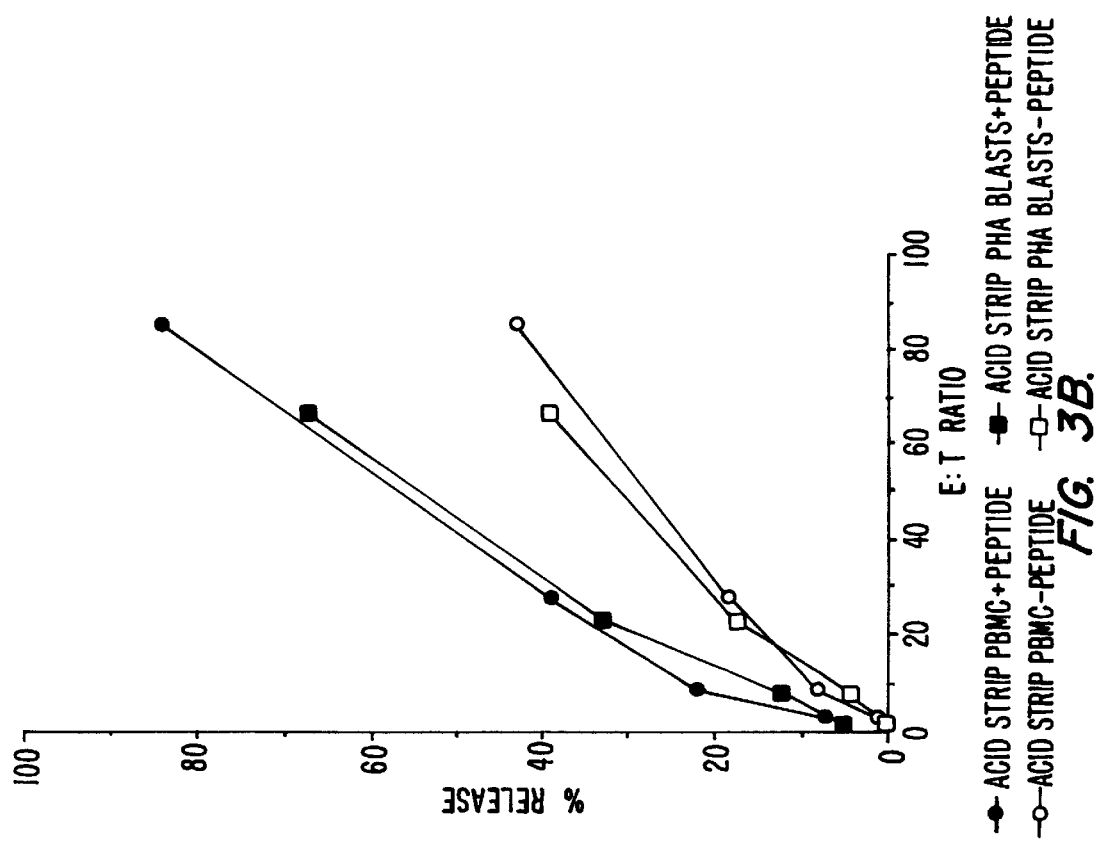
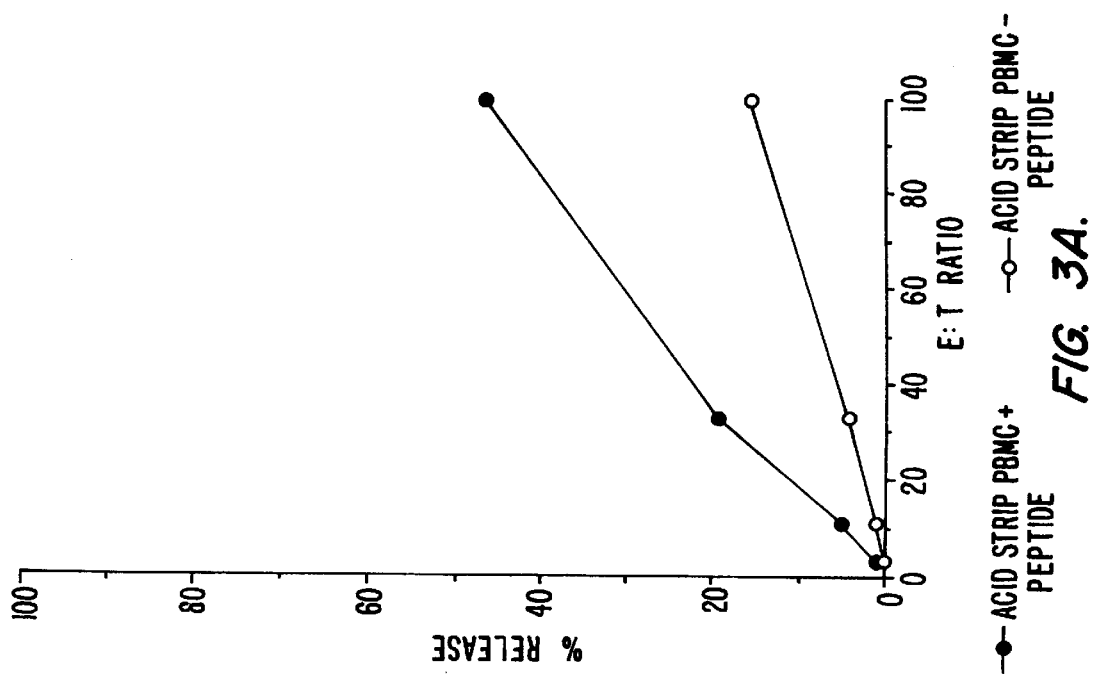

◆ 938-MEL (HLA-A1/24, MAGE1⁺)
◇ 888-MEL (HLA-A1/24, MAGE1⁻)

◆ 938-MEL (HLA-A1/24, MAGE1⁺)
◇ 888-MEL (HLA-A1/24, MAGE1⁻)

METHODS FOR EX VIVO THERAPY USING PEPTIDE-LOADED ANTIGEN PRESENTING CELLS FOR THE ACTIVATION OF CTL

This is a continuation of application Ser. No. 08/103,401, filed Aug. 6, 1993, now abandoned.

BACKGROUND OF THE INVENTION

The present invention relates to compositions and methods for preventing or treating a number of pathological states such as viral diseases and cancer through ex vivo therapy. In particular, it provides methods for inducing cytotoxic T lymphocytes (CTL) using antigen presenting cells (APC) with a peptide of choice bound to selected major histocompatibility complex (MHC) molecules.

Cytotoxic T cells, or CD8 cells as they are also known, represent the main line of defense against viral infections. CTLs specifically recognize and kill cells which are infected by a virus. The T cell receptors on the surface of CTLs cannot recognize foreign antigens directly. In contrast to antibodies, antigen must first be presented to the T cell receptors for activation to occur.

The presentation of antigen to T cells is accomplished by the major histocompatibility complex (MHC) molecules. The major histocompatibility complex (MHC) refers to a large genetic locus encoding an extensive family of glycoproteins which play an important role in the immune response. The MHC genes, which are also referred to as the HLA (human leukocyte antigen) complex, are located on chromosome 6 in humans. The molecules encoded by MHC genes are present on cell surfaces and are largely responsible for recognition of tissue transplants as "non-self".

MHC molecules are classified as either Class I, Class II or class III molecules. Class II MHC molecules are expressed primarily on cells involved in initiating and sustaining immune responses, such as T lymphocytes, B lymphocytes, macrophages, etc. Class II MHC molecules are recognized by helper T lymphocytes and induce proliferation of helper T lymphocytes and amplification of the immune response to the particular immunogenic peptide that is displayed. Class I MHC molecules are expressed on almost all nucleated cells and are recognized by CTLs. T cells that serve mainly as helper cells express CD4 and are primarily restricted to Class II molecules, whereas CD8-expressing cells, represented by cytotoxic effector cells, interact with Class I molecules.

The CTL recognizes the antigen in the form of a peptide fragment bound to the MHC class I molecules rather than the intact foreign antigen itself. The antigen must normally be endogenously synthesized by the cell, and a portion of the protein antigen is degraded into small peptide fragments in the cytoplasm. Some of these small peptides translocate into a pre-Golgi compartment and interact with class I heavy chains to facilitate proper folding and association with the subunit β2 microglobulin. The peptide-MHC class I complex is then routed to the cell surface for expression and potential recognition by specific CTLs. Investigations of the crystal structure of the human MHC class I molecule, HLA-A2.1, indicate that a peptide binding groove is created by the folding of the α1 and α2 domains of the class I heavy chain (Bjorkman et al., Nature, 329:506 ( 1987).

For many years, immunologists have hoped to raise specific cytotoxic cells targeting viruses, retroviruses and cancer cells. One possible approach is to immunize a healthy individual, isolate the CTLs from this individual, and inject these cells into the diseased person. This experimental protocol seems to work in inbred mouse strains, but it has not been successfully tried in humans. For this approach to work the MHC haplotype of the donor must be identical to that of the recipient. This is important because the CTLs of the recipient can only interact with peptides bound to one of the three to six Class I molecules present in the individual. Second, CTLs react violently with all Class I molecules which are different from those expressed in the individual from whom the CD8 cells are obtained, regardless of what peptides the Class I molecules contain. This reactivity is the underlying cause of the immune rejection of transplanted organs.

Because it is difficult to find two unrelated persons with exactly the same Class I molecules, some therapeutic approaches take the non-specific approach of "boosting" existing CD8 cells by incubating them in vitro with IL-2, a growth factor for T cells. However, this protocol (known as LAK cell therapy or TIL [tumor infiltrating lymphocytes] therapy) will only allow the expansion of those CTLs which are already activated. As the immune system is always active for one reason or another, most of the IL-2 stimulated cells will be irrelevant for the purpose of combatting the disease. In fact, it has not been documented that this type of therapy activates any cells with the desired specificity. The benefits of LAK cell therapy are ambiguous at best, and the side effects are often severe. (Greenberg, P. 1991. Adoptive T cell therapy of tumors: Mechanisms operative in the recognition and elimination of tumor cells. Advances in Immunology 49:281. Melief, C. 1992. Tumor eradication by adoptive transfer of cytotoxic T lymphocytes. Adv. Cancer Research 58:14. 34. Riddell, S., K. Watanabe, J. Goodrich, C. Li, M. Agha, P. Greenberg. 1992. Restoration of viral immunity in immunodeficient humans by the adoptive transfer of T cell clones. Science 257:238. ).

The preferred approach for the treatment of such diseases as cancer, AIDS, hepatitis and other infectious disease would be to activate only those CTLs recognizing diseased cells. While various procedures have been applied in these diseases, few if any successful attempts using cytotoxic T cells have been reported. Ex vivo activation of CTLs would be the preferable means of treating the types of disease noted above. However, no reliable procedures have been available to specifically activate CTLs associated with these diseases. The present invention addresses these and other problems.

SUMMARY OF THE INVENTION

This invention is directed to methods of activating cytotoxic T cells (CD8 cells) in vitro or in vivo. The methods of activating CD8 cells comprise: dissociating bound peptides from class I MHC molecules on antigen presenting cells using a mild acid treatment; associating selected immunogenic peptides with the class I MHC molecule on the antigen presenting cell; and incubating the antigen presenting cells with the cytotoxic T cells, thereby producing activated cytotoxic T cells. The methods of the present invention are capable of generating empty MHC class I molecules on antigen presenting cells and in turn inducing CTL and affecting killing of class I matched cells.

The antigen presenting cells having empty MHC class I molecules on their surface are capable of inducing cytotoxic T cells which are useful in the treatment of chronic infectious diseases and cancer. Specifically, this invention provides methods of producing empty MHC class I molecules on antigen presenting cells, loading those empty MHC class I molecules with selected immunogenic peptides, activating cytotoxic T cells which are specific for killing specific antigen targets. This invention has broad therapeutic application in the treatment of cancers, certain immune diseases and viral diseases. As such the method may further comprise: separating activated CTLs from the antigen presenting cells having the empty MHC class I molecule on its surface; suspending the activated CTLs in an acceptable carrier or excipient as a pharmaceutical composition; and administering the pharmaceutical composition to a patient having the disease.

BRIEF DESCRIPTION OF THE DRAWINGS

FIG. 3 shows CTL induction using X351 or X355 A2.1 responders and autologous acid stripped PBMCs or PHA blasts as stimulators after loading with the 1044.04 (PAP 135–143); 1044.05 (PSA 166–175) 1044.06 (PSA 118–128) peptide pool.

DESCRIPTION OF THE PREFERRED EMBODIMENTS

Figure 1A:
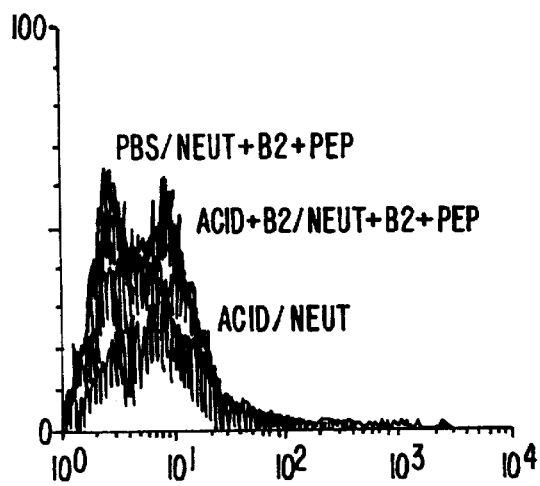
FIG. 1 shows the effects of $\beta_2$microglobulin and exogenous 941.01 (HB$_c$ 18–27) peptide on MHC class I molecules from acid stripped and loaded PHA blasts
Figure 1B:
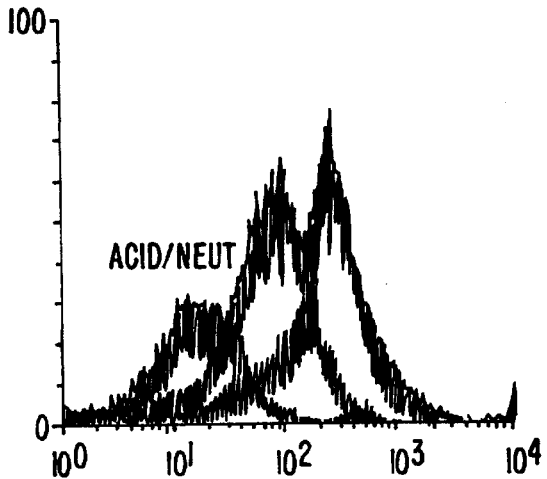
Figure 1C:
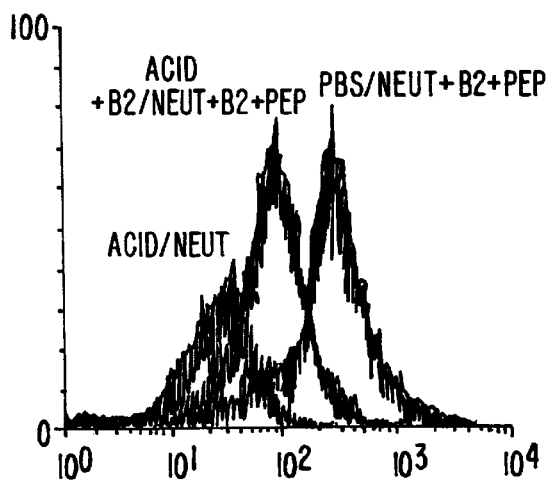
Figure 1D:
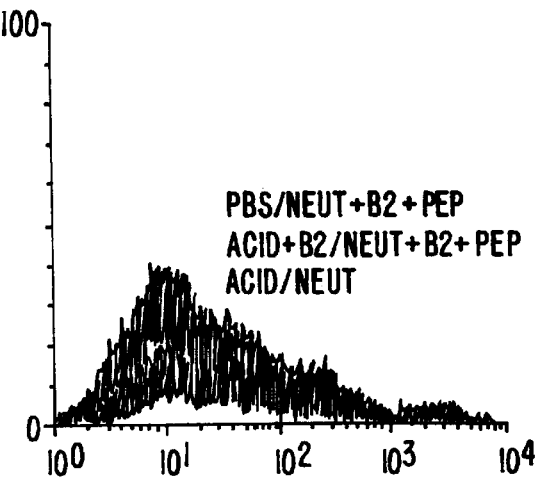

The term "peptide" is used interchangeably with "oligopeptide" in the present specification to designate a series of residues, typically L-amino acids, connected one to the other typically by peptide bonds between the alpha-amino and carbonyl groups of adjacent amino acids.

An "immunogenic peptide" is a peptide which comprises an allele-specific motif such that the peptide will bind the MHC allele and be capable of inducing a CTL response. Thus, immunogenic peptides are capable of binding to an appropriate class I MHC molecule and inducing a cytotoxic T cell response against the antigen from which the immunogenic peptide is derived.

The term "residue" refers to an amino acid or amino acid mimetic incorporated in an oligopeptide by an amide bond or amide bond mimetic.

The present invention relates to methods of enhancing the immune response to various diseases using ex vivo therapy. The general approach of the invention comprises isolation of peripheral blood mononuclear cells (PBMCs) from a patient, loading a desired immunogenic peptide into the binding pockets of MHC class I molecules on the surface of antigen presenting cells (APCs), incubating the APCs with precursor CTLs in the sample to induce proliferation of CTLs recognizing the peptide, and using the CTLs to identify antigenic epitopes and by expanding their numbers introduce the activated CTLs into the patient.

The procedures of the present invention depend in part upon the determination of epitopes recognized by CTLs capable of eliminating target infected cells. One approach to identification of these epitopes is the identification of allele-specific peptide motifs associated with a particular disease for human Class I MHC allele subtypes. The MHC class I antigens are encoded by the HLA-A, B, and C loci. HLA-A and B antigens are expressed at the cell surface at approximately equal densities, whereas the expression of HLA-C is significantly lower (perhaps as much as 10-fold lower). Each of these loci have a number of alleles. A large number of cells with defined MHC molecules, particularly MHC Class I molecules, are known and readily available. These cells can be used to identify particular allele specific motifs associated with target diseases.

The allele-specific motifs are then used to define T cell epitopes from any desired antigen, particularly those associated with human viral diseases or cancers, for which the amino acid sequence of the potential antigen targets is known. This general approach is described in detail in copending and commonly assigned applications U.S. Ser. No. 07/926,666 and U.S. Ser. No. 08/027,146, which are incorporated herein by reference.

Potential epitopes on a number of target proteins can be identified in this manner. Examples of suitable antigens include prostate specific antigen (PSA), hepatitis B core, surface and polymerase antigens (HBVc, HBVs, HBVP), hepatitis C antigens, Epstein-Barr virus antigens, melanoma antigens (e.g., MAGE-1), human immunodeficiency virus (HIV) antigens, human papilloma virus (HPV) antigens, cytomegalovirus (CMV), herpes simplex virus (HSV), and other oncogene products (c-Erb B$_2$, CEA, p 53-breast/ovary).

These approaches typically involve isolation of peptides from a particular MHC molecule and sequencing the peptides to determine the relevant motif. Buus et al., *Science*, 242:1065 (1988) first described a method for acid elution of bound peptides from MHC. Subsequently, Rammensee and his coworkers (Falk et al., *Nature*, 351:290 (1991) developed an approach to characterize naturally processed peptides bound to class I molecules. Other investigators have successfully achieved direct amino acid sequencing of the more abundant peptides in various HPLC fractions by conventional automated sequencing of peptides eluted from B type class I molecules (Jardetzky, et al., Nature, 353:326 (1991) and of the A2.1 type by mass spectrometry (Hunt, et al., *Science*, 225:1261 (1992). A review of the characterization of naturally processed peptides found on MHC Class I molecules is presented by Rötzschke and Falk (Rötzschke and Falk, *Immunol. Today*, 12:447 (1991).

Definition of motifs specific for different class I alleles allows the identification of potential peptide epitopes from an antigenic protein whose amino acid sequence is known. Typically, identification of potential peptide epitopes is initially carried out using a computer to scan the amino acid sequence of a desired antigen for the presence of motifs. The epitopic sequences are then synthesized. The capacity to bind MHC Class molecules is measured in a variety of different ways using, for example, purified class I molecules and radioiodinated peptides and/or cells expressing empty class I molecules by, for instance, immunofluorescent staining and flow microfluorimetry, peptide-dependent class I assembly assays, and inhibition of CTL recognition by peptide competition. Other alternatives described in the literature include inhibition of antigen presentation (Sette, et al., *J. Immunol.*, 141:3893 (1991), in vitro assembly assays (Townsend, et al., *Cell*, 62:285 (1990), and FACS based assays using mutated ells, such as RMA.S (Melief, et al., *Eur. J. Immunol.*, 21:2963 [1991]).

Next, peptides that test positive in the MHC class I binding assay are assayed for the ability of the peptides to induce specific primary or secondary CTL responses in vitro. For instance, antigen-presenting cells that have been incubated with a peptide can be assayed for the ability to induce CTL responses in responder cell populations. For secondary responses, antigen-presenting cells can be normal cells such as peripheral blood mononuclear cells or dendritic cells (Inaba, et al., *J. Exp. Med.*, 166:182 (1987); Boog, *Eur. J. Immunol.*, 18:219 [1988]).

Alternatively, mutant mammalian cell lines that are deficient in their ability to load class I molecules with internally processed peptides, such as the mouse cell lines RMA-S (Kärre, et al. *Nature*, 319:675 (1986); Ljunggren, et al., *Eur. J. Immunol.*, 21:2963–2970 (1991)), and the human somatic T cell hybridoma, T-2 (Cerundolo, et al., *Nature*, 345:449–452 (1990)) and which have been transfected with the appropriate human class I genes are conveniently used, when peptide is added to them, to test for the capacity of the peptide to induce in vitro primary CTL responses. These empty MHC cells are preferable for inducing a primary response since the density of MHC-peptide complexes on the surface of the antigen presenting cell will be greater. Other eukaryotic cell lines which could be used include various insect cell lines such as mosquito larvae (ATCC cell lines CCL 125, 126, 1660, 1591, 6585, 6586), silkworm (ATTC CRL 8851), armyworm (ATCC CRL 1711), moth (ATCC CCL 80) and Drosophila cell lines such as a Schneider cell line that have been transfected with the appropriate human class I MHC allele encoding genes and the human $B_2$ microglobulin genes.

Once the appropriate epitope is determined, immunogenic peptides comprising the motif required for MHC binding and the epitope recognized by the CTL are synthesized. The immunogenic peptides can be prepared synthetically, or by recombinant DNA technology or isolated from natural sources such as whole viruses or tumors. One of skill will recognize that the immunogenic peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. When possible, it may be desirable to optimize peptides of the invention to a length of 9 or 10 amino acid residues, commensurate in size with endogenously processed viral peptides or tumor cell peptides that are bound to MHC class I molecules on the cell surface.

Peptides having the desired activity may be modified as necessary to provide certain desired attributes, e.g., improved pharmacological characteristics, while increasing or at least retaining substantially all of the biological activity of the unmodified peptide to bind the desired MHC molecule and activate the appropriate T cell. For instance, the peptides may be subject to various changes, such as substitutions, either conservative or non-conservative, where such changes might provide for certain advantages in their use, such as improved MHC binding. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well known peptide synthesis procedures.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984), supra.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, New York (1982), which is incorporated herein by reference. Fusion proteins which comprise one or more peptide sequences of the invention can also be used to present the appropriate T cell epitope.

The immunogenic peptides are then used to activate CTL ex vivo. The ex vivo therapy methods of the present invention and pharmaceutical compositions thereof are useful for treatment of mammals, particularly humans, to treat and/or prevent viral infection, immune disorders and cancer. Examples of diseases which can be treated using the ex vivo therapy methods of the invention include prostate cancer, hepatitis B, hepatitis C, AIDS, renal carcinoma, cervical carcinoma, lymphoma, CMV, condyloma acuminatum breast and ovarian cancer, colon, lung cancer and HSV.

For therapeutic use, therapy should begin at the first sign of viral infection or the detection or surgical removal of tumors or shortly after diagnosis in the case of acute infection. This is followed by boosting levels of CTL at least until symptoms are substantially abated and for a period thereafter. In chronic infection, loading doses followed by boosting doses may be required.

Treatment of an infected individual with the methods of the invention may hasten resolution of the infection in acutely infected individuals. For those individuals susceptible (or predisposed) to developing chronic infection the methods are useful for preventing the evolution from acute to chronic infection. Where the susceptible individuals are identified prior to or during infection, the compositions can be targeted to them, minimizing the need for administration to a larger population.

The methods of the present invention can also be used for the treatment of chronic infection and to stimulate the immune system to eliminate virus-infected cells in carriers.

Ex vivo CTL responses to a particular pathogen (infectious agent or tumor antigen) are induced by incubating in tissue culture the patient's CTL precursor cells (CTLP) together with a source of antigen-presenting cells (APC) loaded with the appropriate immunogenic peptide. After an appropriate incubation time (typically 3–12 weeks) in which the CTLp are activated and mature and expand into effector CTL, the cells are infused back into the patient, where they will destroy their specific target cell (an infected cell or a tumor cell). Infusion of the cells into the patient may include a T cell growth factor such as interleukin 2 (IL-2). In order to optimize the in vitro conditions for the generation of specific cytotoxic T cells, the culture of stimulator cells is maintained in an appropriate serum-free medium which may include one or more growth factors such as IL-2, IL-4, IL-7 and IL-12.

Peripheral blood lymphocytes are conveniently isolated following simple venipuncture or leukapheresis of normal donors or patients and used as the responder cell sources of CTLP. In one embodiment particularly for secondary CTL responses, the appropriate APC are incubated with 10–100 $\mu$M of peptide in serum-free media for 4 hours under appropriate culture conditions. The peptide-loaded APC are then incubated with the responder cell populations in vitro for 7 to 10 days under optimized culture conditions. For primary CTL induction, APC expressing empty MHC would be used to stimulate naive CTLP. In this case the CTL would be stimulated more frequently (1–2 times).

Positive CTL activation can be determined by assaying the cultures for the presence of CTLs that kill radiolabeled target cells, both specific peptide-pulsed targets as well as target cells expressing endogenously processed form of the relevant virus or tumor antigen from which the peptide sequence was derived.

Specificity and MHC restriction of the CTL of a patient can be determined by a number of methods known in the art. For instance, CTL restriction can be determined by testing against different peptide loaded target cells expressing human MHC class I alleles shared with the HLA phenotype of the donor CTL. The peptides that test positive in the MHC binding assays and give rise to specific CTL responses are identified as immunogenic peptides.

As mentioned above, the induction of CTL in vitro requires the specific recognition of peptides that are bound to allele specific MHC class I molecules on APC. The number of specific MHC/peptide complexes per APC determines the level of stimulation of CTL, particularly during the primary immune response. While small amounts of peptide/MHC complexes per cell are sufficient to render a cell susceptible to lysis by CTL, or to stimulate a secondary CTL response, the successful activation of a CTLp during primary response requires a significantly higher number of MHC/peptide complexes.

Since mutant cell lines capable of expressing empty MHC do not exist for every human MHC allele, it is advantageous to use a technique to remove endogenous NHC-associated peptides from the surface of APC, followed by loading the resulting empty MHC molecules with the immunogenic peptides of interest. The use of non-transformed (non-tumorigenic), non-infected cells, and preferably, autologous cells of patients as APC is desirable for the design of CTL induction protocols directed towards development of ex vivo CTL therapies. This present invention provides novel methods generating empty class I MHC which can then be loaded with an appropriate immunogenic peptide by stripping the endogenous MHC-associated peptides from the surface of APC or through cold temperature incubation (37° C.→26° C.)followed by the loading of desired peptides.

A stable MHC class I molecule is a trimeric complex formed of the following elements: 1) a peptide usually of 8–10 residues, 2) a transmembrane heavy polymorphic protein chain which bears the peptide-binding site in its $\alpha$1 and $\alpha$2 domains, and 3) a non-covalently associated non-polymorphic light chain, $\beta_2$microglobulin. Removing the bound peptides and/or dissociating the $\beta_2$microglobulin from the complex renders the MHC class I molecules nonfunctional and unstable, resulting in rapid degradation at 37° C. Almost all MHC class I molecules isolated from PBMCs have endogenous peptides bound to them. Therefore, the first step to prepare APC for primary CTL induction is to remove all endogenous peptides bound to MHC class I molecules on the APC without causing degradation or cell death before exogenous peptides can be added.

Two possible ways to generate free MHC class I molecules include lowering the culture temperature from 37° C. to 26° C. overnight to allow MHC class I without peptides to be expressed and stripping the endogenous peptides from the cell using a mild acid treatment. The mild acid treatment releases previously bound peptides into the extracellular environment allowing new exogenous peptides to bind to the empty class I molecules. The overnight cold-temperature incubation at 26° C. which may slow the cell's metabolic rate enables expression of stable empty class I molecules which then bind exogenous peptides efficiently. It is also likely that cells not actively synthesizing MHC molecules (e.g., resting PBMC) would not produce high amounts of empty surface MHC molecules by the cold temperature procedure.

Extraction of the peptides is accomplished by harsh acid stripping using trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes (31. Storkus, W., H. Zeh, R. Salter, and M. Lotze. 1993. Identification of T cell epitopes: Rapid isolation of class I-presented peptides from viable cells by mild acid elution [submitted]). The treatment is especially effective, in that only the MHC class I molecules are destabilized (and associated peptides released), while other surface antigens remain intact, including MHC class II molecules. (16. Suguwara, S., T. Abo, and K. Kumagai. 1987. A simple method to eliminate the antigenicity of surface class I MHC molecules from the membrane of viable cells by acid treatment at pH 3. J. Immunol. Meth. 100:83). Most importantly, treatment of cells with the mild acid solutions do not affect the cell's viability or metabolic state. The mild acid treatment is rapid since the stripping of the endogenous peptides occurs in two minutes at 4° C. and the APC is functional after the appropriate peptides are loaded. The technique is utilized herein to make peptide-specific APCs for the generation of primary antigen-specific CTL. The resulting APCs are efficient in inducing peptide-specific CTL.

Typically in a primary response prior to incubation of the APCs with the CTLP to be activated, an amount of antigenic peptide is added to the APCs or stimulator cell culture, of sufficient quantity to become loaded onto the human Class I molecules to be expressed on the surface of the APCS. In the present invention, a sufficient amount of peptide is an amount that will allow about 200 or more human Class I MHC molecules loaded with peptide to be expressed on the surface of each stimulator cell. Preferably, the stimulator cells are incubated with 5–10µg/ml peptide.

Resting or precursor CTLs are then incubated in culture with the appropriate APCs for a time period sufficient to activate the CTLs. The CTLs are activated in an antigen-specific manner. The ratio of precursor CTLs to APCs may vary from individual to individual and may further depend upon variables such as the amenability of an individual's lymphocytes to culturing conditions and the nature and severity of the disease condition or other condition for which the within-described treatment modality is used. Preferably, however, the CTL:APC (i.e. responder to stimulator) ratio is in the range of about 10:1 to 100:1. The CTL/APC culture may be maintained for as long a time as is necessary to stimulate a therapeutically useable or effective number of CTL.

Activated CTL may be effectively separated from the APC using one of a variety of known methods. For example, monoclonal antibodies specific for the APCs, for the peptides loaded onto the stimulator cells, or for the CTL (or a segment thereof) may be utilized to bind their appropriate complementary ligand. Antibody-tagged cells may then be extracted from the admixture via appropriate means, e.g., via well-known immunoprecipitation or immunoassay methods.

Effective, cytotoxic amounts of the activated CTLs can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CTLS are utilized for adult humans, compared to about $5 \times 10^6 – 5 \times 10^7$ cells used in mice.

As discussed above, the activated CTLS may be harvested from the cell culture prior to administration of the cells to the individual being treated. It is important to note, however, that unlike other present treatment modalities, the present method uses a cell culture system that does not contain transformed or tumor cells. Therefore, if complete separation of antigen-presenting cells and activated CTLS is not achieved, there is no inherent danger known to be associated with the administration of a small number of stimulator cells, whereas administration of mammalian tumor-promoting cells may be extremely hazardous.

One embodiment of the present invention uses the APC generated by the in vitro techniques of this application for therapy against CTL in vivo. In this embodiment, the APC are a patient's cells (e.g., the peripheral blood cells) which are stripped of their natural antigenic peptides and loaded with a peptide of choice which is conjugated to a toxin (e.g. ricin A chain or pseudomonas toxin). The APCs are then re-introduced into the patient, where they will be bound by the endogenous CTLs that are specific for the antigenic peptide. The coupled toxin will kill the activated CTL that are harmful i.e. those which stimulate transplant rejection after it binds the APC. Such directed CTL killing is broadly useful for treating tissue-transplantation rejection and auto-immune disorders, which are mediated through CTL. The treatment regime will vary depending upon the specific disorder to be treated and the judgement of the treating physician.

Methods of re-introducing cellular components are known in the art and include procedures such as those exemplified in U.S. Pat. No. 4,844,893 to Honsik, et al. and U.S. Pat. No. 4,690,915 to Rosenberg, which are incorporated herein by reference. For example, administration of activated CTLs via intravenous infusion is appropriate.

The following examples are offered by way of illustration, not by way of limitation.

EXAMPLE 1

Ex vivo induction of Cytotoxic T Lymphocytes (CTL)

Peripheral blood mononuclear cells (PBMC) are isolated from an HLA-typed patient by either venipuncture or leukapheresis (depending upon the initial amount of CTLP required), and purified by gradient centrifugation using Ficoll-Paque (Pharmacia). Typically, one can obtain one million PBMC for every ml of peripheral blood, or alternatively, a typical leukapheresis procedure can yield up to a total of $1-10 \times 10^{10}$ PBMC.

The isolated and purified PBMC are co-cultured with an appropriate number of APC expressing empty MHC molecules, previously incubated ("pulsed") with an appropriate amount of synthetic peptide (containing the HLA binding motif and the sequence of the antigen in question). PBMC are usually incubated at $1-3 \times 10^6$ cells/ml in culture medium such as RPMI-1640 (with autologous serum or plasma) or the serum-free medium AIM-V (Gibco).

APC are usually used at concentrations ranging from $1 \times 10^4$ to $1 \times 10^6$ cells/ml, depending on the type of cell used. Possible sources of APC include: autologous PBMCs, SAC-I activated PBMCs, PHA blasts; autologous dendritic cells (DC) which are isolated from PBMC and purified as described (Inaba, et al., *J. Exp. Med.*, 166:182 (1987)); and mutant and genetically engineered mammalian cells such as the mouse RMA-S cell line or the human T2 cell line transfected with the appropriate MHC genes that express "empty" HLA molecules which are syngeneic to the patient's allelic HLA form). APC containing empty HIA molecules are known to be potent inducers of CTL responses, possibly because the peptide can associate more readily with empty MHC molecules than with MHC molecules which are occupied by other peptides (DeBruijn, et al., *Eur. J. Immunol.*, 21:2963–2970 (1991)).

The APC are gamma irradiated with an appropriate dose (using, e.g., radioactive cesium or cobalt) to prevent their proliferation and to facilitate the expansion of the CTLp.

The mixture cultures, containing PBMC, APC and peptide are kept in an appropriate culture vessel such as plastic T-flasks, gas-permeable plastic bags, or roller bottles, at 37° centigrade in a humid air/$CO_2$ incubator. After the activation phase of the culture, which usually occurs during the first 3–5 days, the resulting effector CTL can be further expanded, by the addition of recombinant growth factors such as interleukin-2 (IL-2), interleukin-4 (IL-4), or interleukin-7 (IL-7) to the cultures. An expansion culture can be kept for an additional 5 to 12 days, depending on the numbers of effector CTL required for a particular patient. In addition, expansion cultures may be performed using hollow fiber artificial capillary systems (Cellco), where larger numbers of cells (up to $1 \times 10^{11}$) can be maintained. In order to obtain the required cell numbers for treatment, it may be necessary to restimulate the cultures 2–4 times with irradiated, autologous, peptide pulsed adherent PBMCs.

Before the cells are infused into the patient, they are tested for activity, viability, toxicity and sterility. The cytotoxic activity of the resulting CTL can be determined by a standard $^{51}$Cr-release assay (Biddison, W. E. 1991, Current Protocols in Immunology, p7,17.1–7.17.5, Ed. J. Coligan et al., J. Wiley and Sons, New York), using target cells that express the appropriate HLA molecule, in the presence and absence of the immunogenic peptide. Viability is determined by the exclusion of trypan blue dye by live cells. Cells are tested for the presence of endotoxin by conventional techniques. Finally, the presence of bacterial or fungal contamination is determined by appropriate microbiological methods (chocolate agar, etc.). Once the cells pass all quality control and safety tests, they are washed and placed in the appropriate infusion solution (Ringer/glucose lactate/human serum albumin) which may include a T-cell growth factor such as IL-2 and infused intravenously into the patient.

EXAMPLE 2

Preparation of Effective HLA Allele-Specific Antigen Presenting Cells by Acid Stripping Followed By Peptide Loading This example demonstrates the use of cold temperature incubation and acid stripping for generation of empty MHC class I molecules to enable peptide loading method to prepare effective HLA-allele-specific antigen presenting cells (APC) for use in diagnostic or ex vivo therapy applications. The APC in this example were used to sensitize precursor cytotoxic T lymphocytes for the development of antigen-specific cytotoxic cells. This was accomplished using either staphylococcus aureus cowan I SAC I activated PBMC, phytohemagglutinin (PHA) T-cell blasts or peripheral blood mononuclear cells (PBMC) as APC in the HLA-A2.1 and HLA-A1 systems. The results are applicable to other APC and to the other MHC alleles.

Culture Medium. PHA blasts and CTL inductions were done in RPMI 1640+Hepes+glutamine (Gibco) supplemented with 2 mM L-glutamine (Irvine Scientific), 50 µg/ml gentamicin (Gibco), and 5% heat inactivated pooled human Type AB serum (Gemini Bioproducts) [RPMI/5% HS]. EBV transformed lymphoblastoid cell lines (LCL) were maintained in RPMI 1640+Hepes+glutamine (BioWhittaker) supplemented with L-glutamine and gentamicin as above and 10% heat inactivated fetal calf serum (Irvine Scientific) [RPMI/10% FCS]. Chromium release assays were performed in RPMI/10% FCS.

Cytokines. Recombinant human interleukin-2 (rIL-2) (Sandoz) was used at a final concentration of 10 U/ml. Recombinant human interleukin-7 (rIL-7) (Genzyme) was used at a final concentration of 10 ng/ml.

Cultured Cell Lines. JY, a HLA A2.1 expressing human EBV-transformed B-cell line, was grown in RPMI/10% FCS. K562, a NK cell sensitive erythroblastoma line was grown in RPMI/10% FCS. K562 was used to reduce background killing by NK and LAK cells in the chromium release assays.

Peptides. The immunogenic peptides used in these studies were synthesized as described above using motifs for HLA alleles for specific target antigens as described in detail in copending and commonly assigned applications U.S. Ser. No. 07/926,666 and U.S. Ser. No. 08/027,146 and their sequences are shown in Table 1. Peptides were routinely dissolved in 100% DMSO at 20 mg/ml, aliquoted, and stored at −20° C.

Isolation of Peripheral Blood Mononuclear Cells (PBMC). Whole blood was collected in heparin (10 U/ml) containing syringes and spun in 50cc conical centrifuge tubes (Falcon) at 1600 rpm (Beckman GS-6KR) 15 min. The plasma layer was then removed and 10 ml of the buffy coat collected with a 10 ml pipette using a circular motion. The buffy coat was mixed thoroughly and diluted with an equal volume of serum free RPMI 1640. The diluted buffy coat was then layered over 20 ml Ficoll-Paque (Pharmacia) in a 50cc conical tube and centrifuged 400× g for 20 minutes at room temperature without the brake off. The interface containing the PBMCs was collected using a transfer pipet (two interfaces per 50cc tube) and washed three times with 50 ml serum free RPMI (1700, 1500, and 1300 rpm for 10 minutes.

Freezing and Thawing PBMC. PBMC were frozen at $30 \times 10^6$ cells/ml of 90% FCS+10% DMSO (Sigma) in 1 ml aliquots using cryovials (Nalge). Cryovials were placed in Cryo 1° C. freezing containers (Nalge) containing isopropanol (Fisher) and placed at −70° C. from 4 hours (minimum) to overnight (maximum). Isopropanol was changed after every 5 uses. Cryovials were transferred to liquid nitrogen for long term storage. PBMC were thawed by continuous shaking in a 37° C. water bath until the last crystal was nearly thawed. Cells were immediately diluted into serum free RPMI medium containing DNAse 30 µg/ml (to avoid clumping by dead cells) (Calbiochem) and washed twice.

Preparation of CD4+ T cell depleted responder cell population. CD4+ lymphocyte depletion was performed using antibody-coated flasks: MicroCELLector T-150 flasks for the selection of CD4+ cells (Applied Immune Sciences) were washed according to the manufacturer's instructions with 25 ml PBS CMF (calcium magnesium free)+1 mM EDTA (Sigma) by swirling flasks for 30 sec followed by incubation for 1 hour at room temperature on a flat surface. Buffer was aspirated and flasks were washed 2 additional times by shaking the flasks for 30 seconds and maintaining coverage of the binding surface. To each washed flask, 25 ml culture medium were added and incubated for 20 minutes at room temperature on a flat surface. Media was left in the flask until it was ready to receive the cells. PBMC were thawed in culture medium containing 30 µg/ml DNAse and washed twice. For one flask a maximum of $12 \times 10^7$ cells were resuspended in 25 ml culture medium. Culture medium was aspirated from the flask and then the cell suspension was gently added to the MicroCELLector. Flasks containing the cells were incubated for 1 hour at room temperature on a flat surface. At the end of the incubation, the flask was gently rocked from side to side for 10 seconds to resuspend the nonadherent cells. Nonadherent CD4+ T cell depleted cells were harvested and then flasks were washed twice with PBS CMF to collect the nonadherent cells. Harvested CD4+ T cell depleted cells were pelleted by centrifugation and resuspended in culture medium.

Generation of PHA Blasts. PBMC were isolated using the standard Ficoll-Paque protocol. Frozen cells were washed twice before use. Cells were cultured at $2 \times 10^6$/ml in RPMI/5% HS containing 1 µg/ml PHA (Wellcome) and 10 U/ml rIL-2. PHA blasts were maintained in culture medium containing 10 U/ml rIL-2 with feeding and splitting as needed. PHA blasts were used as APCs on day 6 of culture. Generation of empty class I molecules and peptide loading was only performed by the acid strip method when using PBMCs as APCs.

Acid Stripping/Peptide Loading of PBMC and PHA Blasts. PBMC were isolated using the Ficoll-Paque protocol. When using frozen cells, PBMC were washed twice before using. PHA blasts were prepared as previously described and washed twice before using. Once cells were prepared, they were washed once in cold sterile 0.9% NaCl (J. T. Baker) +1% BSA. In a 50 cc conical centrifuge tube, the cells were resuspended at $10^7$/ml in cold sterile citrate-phosphate buffer [0.13M citric acid (J. T. Baker), 0.06M sodium phosphate monobasic (Sigma) pH 3, 1% BSA, 3 µg/ml β$_2$microglobulin (Scripps Labs)] and incubated for 2 minutes on ice. Immediately, 5 volumes of cold sterile neutralizing buffer #1 [0.15M sodium phosphate monobasic pH 7.5, 1% BSA, 3 µg/ml β$_2$microglobulin, 10 βg/ml peptide] were added, and the cells were pelleted at 1500 rpm, 5 min at 4° C. Cells were resuspended in 1 volume cold sterile neutralizing buffer #2 [PBS CMF, 1% BSA, 30 µg/ml DNAse, 3 µg/ml β$_2$microglobulin, 40 µg/ml peptide] and incubated for 4 hours at 20° C. Cells were diluted with culture medium to approximately $5\times10^6$/ml and irradiated with 6000 rads. Cells were then centrifuged at 1500 rpm for 5 minutes at room temperature and resuspended in culture medium. The acid stripped/peptide loaded cells were used immediately in the CTL induction cultures (below).

Binding Assays Using Intact Cells and Radiolabelled Peptide. JY cells were either acid stripped (i.e. treated with citrate-phosphate buffer and neutralizing buffer #1 as described above) or incubated at a reduced temperature. JY control cells were left untreated in tissue culture media. After treatment both cell populations were washed twice with serum free RPMI and loaded with $^{125}$I-radiolabelled 941.01 (HBc 18–27) peptide (standard chloramine T iodination). To determine binding specificity, $2\times10^6$ cells were resuspended in 200 µl neutralizing buffer #2 (described above) containing $^{125}$I-941.01 ($10^5$ cpms) +/−100 µg unlabelled 941.01. Cells were incubated for 4 hours at 20° C. and washed twice with serum free RPMI to remove free peptide. Cells were resuspended in 200 µl of serum free RPMI. In a microfuge tube the cell suspension was layered over an 800 µl FCS and pelleted by centrifugation for 5 seconds. Supernatants were aspirated and the radioactivity remaining in the pellet was measured (Micromedic automatic gamma counter, 1 minutes per tube).

Binding of Radiolabeled Peptides to Empty MHC Molecules. To determine the efficiency of peptide loading using the cold temperature incubation or acid stripping peptide loading protocol, JY cells (an HLA-A2.1 EBV-transformed B cell line) were preincubated at 26° C. overnight or acid-stripped to remove the endogenous MHC-associated peptides and the loading of exogenous peptide was determined using a $^{125}$I-radiolabelled HLA-A2.1 binding peptide. The specificity of this reaction was determined by measuring the inhibition of labelled peptide binding using a cold peptide of the same sequence. Results presented in Table 2 demonstrate that acid-treatment of the cells increased significantly (approximately 10-fold) the amount of labelled peptide binding to the JY cells. Furthermore, the binding of labelled peptide was completely blocked by the addition of the cold peptide, demonstrating specific binding (data not shown).

FACS Analysis. Approximately $10^6$ cells were used for each antibody that was to be tested. Cells were washed twice with PBS CMF+0.1% BSA. To each sample, 100 µl PBS CMF+ 0.1% BSA+primary antibody at 2 µg/ml (BB7.2, ATCC) or (9.12.1, INSERM-CNRS, Marseille) or (LB3.1, Children's Hospital, Pittsburgh) were added. A negative control was always included. Cells were incubated on ice for 20 minutes and washed twice with PBS CMF+0.1% BSA. Cells were resuspended in 100 µl anti-mouse IgG FITC conjugate (Sigma), diluted 1:50 in PBS CMF+0.1% BSA, and incubated 20 minutes on ice. Cells were washed twice with PBS CMF+0.1% BSA, and resuspended in PBS for FACScan (Becton Dickinson) analysis. When it was necessary to postpone analysis to the subsequent days, the cells were fixed with PBS/1% paraformaldehyde (Fisher) and analyzed within one week.

Measurements by FACS Analysis. PHA-induced T-cell blasts were acid stripped/peptide loaded according to the methods described above. The resulting cells were stained for FACS analysis using anti-HLA-A2 (BB7.2) and anti-HLA alpha chain-specific (9.12.1) monoclonal antibodies. Controls for this experiment included the same cell population which was not treated at pH 3 (but treated with PBS buffer at pH 7.2), and cells treated with citrate-phosphate buffer (to strip the MHC) but neutralized in the absence of β$_2$microglobulin and peptide. The results presented in FIG. 1, indicate that treatment of these cells with the citrate-phosphate (pH3) buffer significantly reduced (10-fold) the reactivity of the cells toward both anti-HLA class I antibodies alone (anti-HLA-A2 and the alpha chain specific), but not towards a monoclonal antibody specific for class II MHC molecules (anti-HLA-DR). Most importantly, neutralization of the acid-stripped cells in the presence of β$_2$microglobulin and peptide resulted in preservation of a significant amount of class I MHC antibody-reactive sites, with only a 2.5-fold decrease in fluorescence intensity. The acid-treated cells remained viable, as measured by trypan blue exclusion and forward/lateral FACS scatter analysis. Similar results were obtained using EBV-transformed B cell lines, fresh (or frozen) PBMC and other peptides (which bind to either HLA-A2.1 or HLA-Al) (data not shown).

Induction of Primary CTL using Acid Stripped/Peptide Loaded Autologous PBMCs or PHA Blasts as Stimulators. Acid stripping/peptide loading of PBMC and PHA blasts are described above. During the 4 hour incubation of stimulator cells with peptide, the responder cell population was prepared: Responders were PBMC that were depleted of CD4+ T cells (described above). Responder cells were resuspended in culture medium at $3\times10^6$/ml and 1 ml of the responder cell suspension was dispensed into each well of a 24-well tissue culture plate (Falcon, Becton Dickinson). The plates were placed in the incubator at 37° C., 5% CO$_2$ until the stimulator population was ready. Once irradiated, stimulator APCs were resuspended in culture medium containing 20 ng/ml rIL-7 at $10^6$/ml for the PBMC, or at $3\times10^5$/ml for the PHA blasts, 1 ml of stimulator cell suspension was added per well to the plates containing the responders. On day 7 after induction, 100 µl culture medium containing 200 ng/ml rIL-7 was added to each well (10 ng/ml rIL-7 final). On day 10 after induction, 100 µl of culture medium containing 200 U/ml rIL-2 was added to each well (10 U/ml rIL-2 final).

Antigen Restimulation of CTL. On day 12–14 after the induction, the primary CTL were restimulated with peptide using autologous, adherent APCs. Autologous PBMC were thawed and washed as described above. Cells were irradiated at 6000 rads. Cells were pelleted and resuspended in culture medium at $4\times10^6$/ml and 1 ml of cell suspension was added to each well of a 24-well tissue culture plate, and incubated for 2 hours at 37° C., 5% CO$_2$. Nonadherent cells were removed by washing each well three times with serum free RPMI. After this step, a 0.5 ml culture medium containing 3 µg/ml β$_2$microglobulin and 20 µg/ml total peptide was added to each well. APC were incubated for 2 hrs at 37° C., under 5% CO$_2$ with the peptide and β$_2$microglobulin. Wells were aspirated and 1 ml of responder cells at $1.5\times10^6$/ml in culture medium was added to each well. After 2 days, 1 ml of culture medium containing 20 U/ml rIL-2 was added to each well. Cultures were supplemented with 10 U/ml rIl-2 (final) every three days thereafter.

Cytotoxicity Chromium Release Assay. Seven days following restimulation of primary induction, the cytotoxic activity of the cultures was assessed.

a. Effector Cell Preparation: The responders were centrifuged and resuspended at $10^7$/ml in RPMI/10% FCS. Threefold serial dilutions of effectors were performed to yield effector to target ratios of 100:1, 33:1, 11:1, and 3:1. Effector cells were aliquoted at 100 μl/well on 96 well U-bottomed cluster plates (Costar), in duplicate.

b. Target Cell Preparation: Approximately 16–20 hours prior to the assay, target cells were resuspended at $3\times10^5$/ml in RPMI/10% FCS in the presence or absence of 3 μg/ml $\beta_2$microglobulin and 10 μg/ml total peptide. After preincubation, target cells were centrifuged and pellets were resuspended in 200 μl (300 μCi) sodium ($^{51}$Cr) chromate (NEN). Cells were incubated at 37° C. for 1 hour with agitation. Labelled target cells were washed 3 times with RPMI/10% FCS.

c. Setting-Up the Assays: Target cell concentration was adjusted to $10^5$/ml in RPMI/10% FCS and 100 μl aliquots were added to each well containing responders. K562 cells (cold targets, to block NK, and LAK activity) were washed and resuspended in RPMI/10% FCS at $10^7$/ml. Aliquots of 20 μl were added per well, yielding a 20:1 cold K562 target to labelled target ratio. For the determination of the spontaneous $^{51}$Cr release, 100 μl/well of RPMI/10% FCS were added to 100 μl/well of labelled target cells, and 20 μl/well of K562. For maximum $^{51}$Cr release, 100 μl 1% Triton X-100 (Sigma) in PBS CMF, was added to the 100 μl/well labelled target cells, and 20 μl/well K562. Plates were centrifuged for 2 minutes at 1200 rpm to accelerate cell conjugate formation. Assays were incubated for 5 hours at 37° C., 5% $CO_2$. Assays were harvested by centrifuging plates for 5 minutes at 1200 rpm and collecting 100 μl/well of supernatant. Standard gamma counting techniques were used to determine percent specific lysis (Micromedic automatic gamma counter, 0.5 minutes per tube). Percent specific lysis was determined by the following formula: cpm experimental release -cpm spontaneous release/cpm maximum release-cpm spontaneous release×100.

Figure 2:
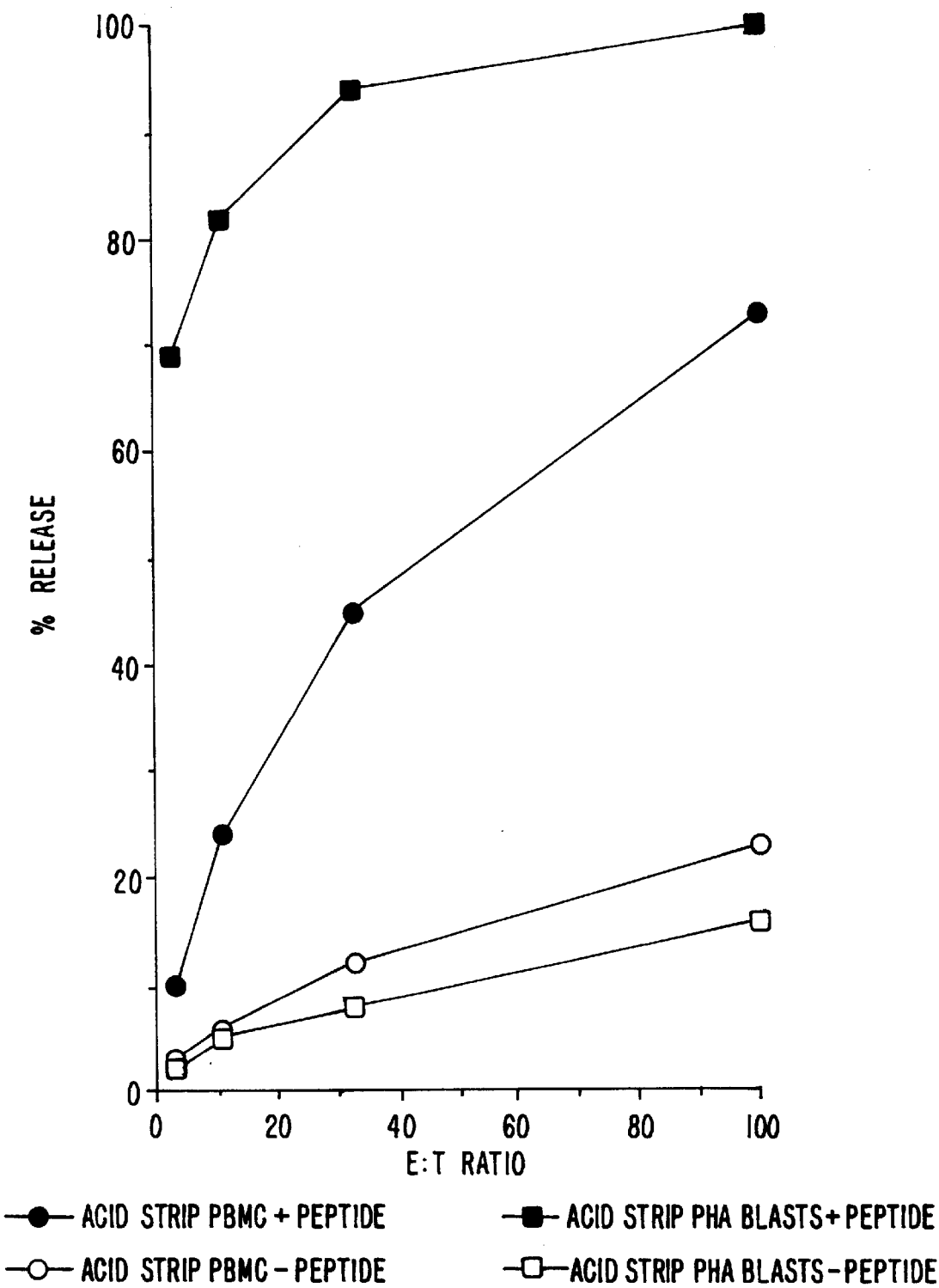
FIG. 2 shows CTL induction using GC43 A2.1 responders and autologous acid-stripped PBMCs or PHA blasts loaded with the 777.03 (HB$_s$ 20–28); 924.07 (HB$_c$ 18-27); 927.32 (HB$_p$ 61–69) peptide pool.
Figure 4:
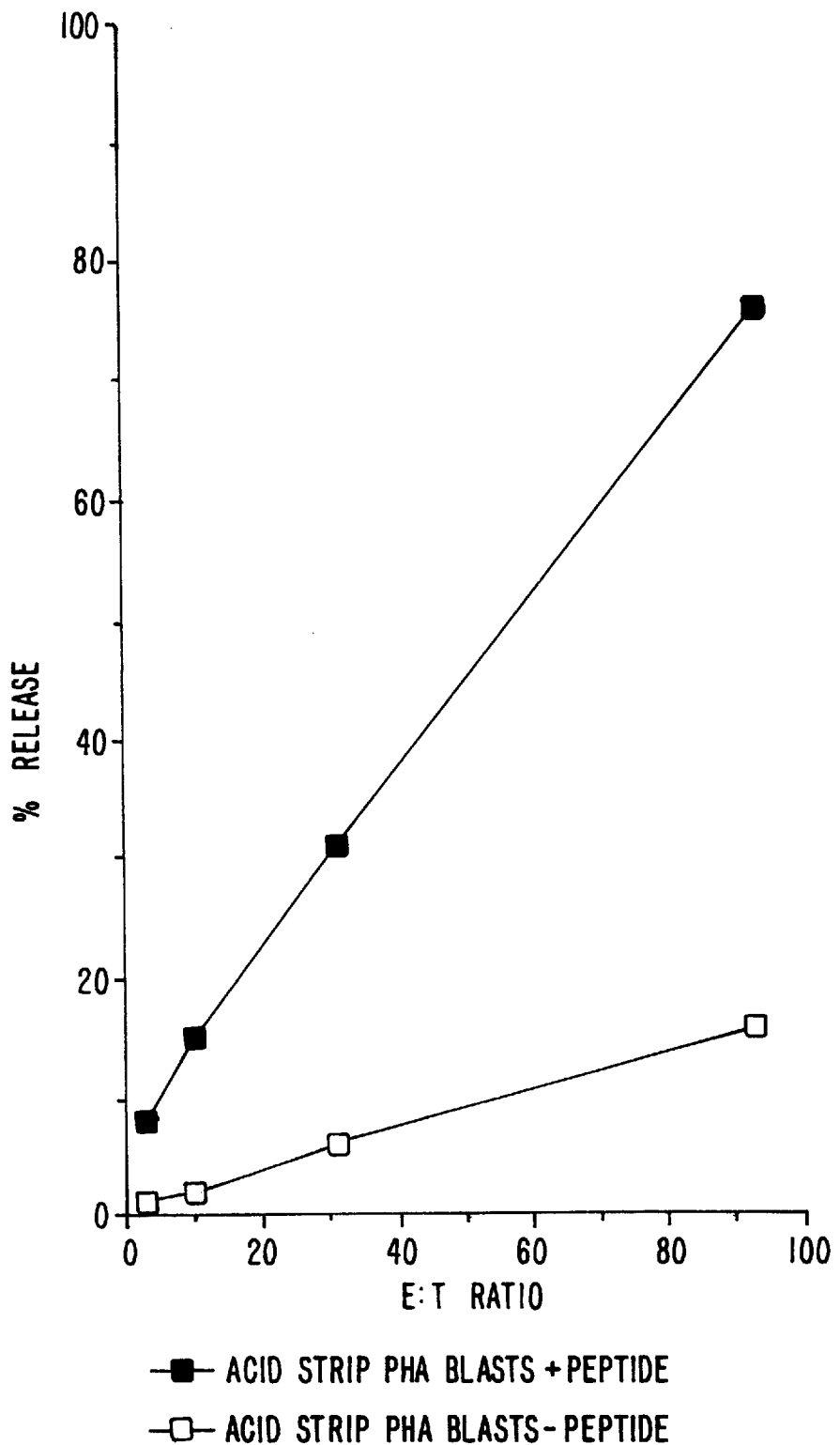
FIG. 4 shows CTL induction using GC49 A2.1 responders and Autologous Acid stripped PHA blasts as stimulators after loading with 939.03 (PSA 49–57) peptide.
Figure 5A:
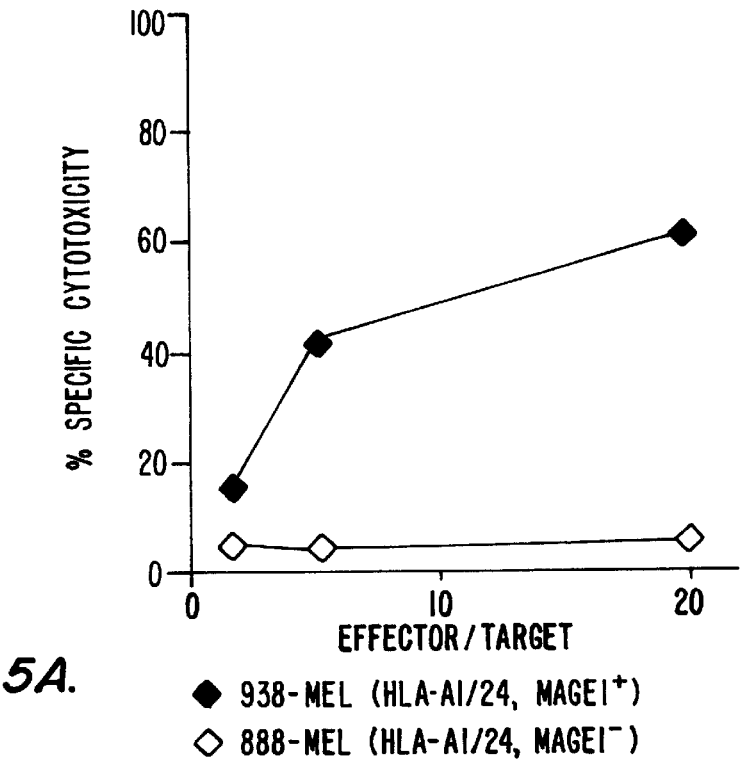
FIG. 5 shows CTL induction using GC66 A1 responders and autologous acid stripped PBMCs as stimulators after loading of peptide 958.01 (MAGE 1:161–169).
Figure 5B:
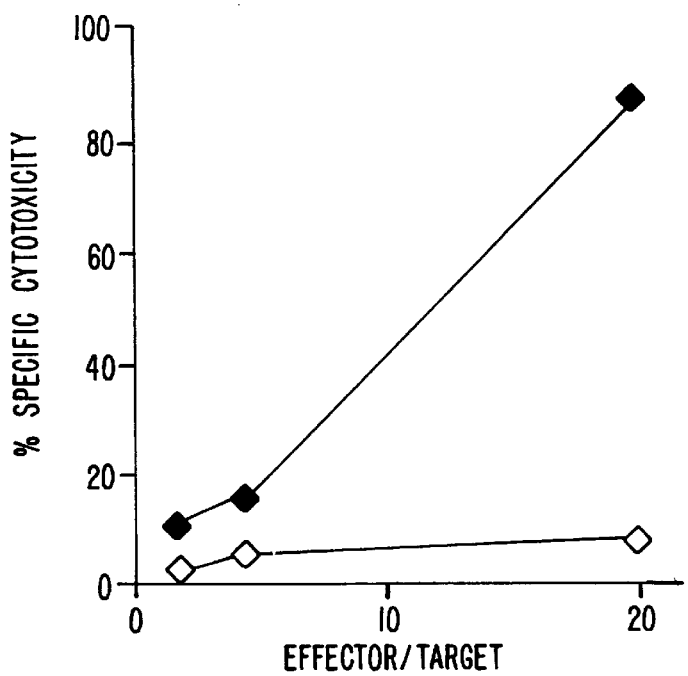
Figure 7A:
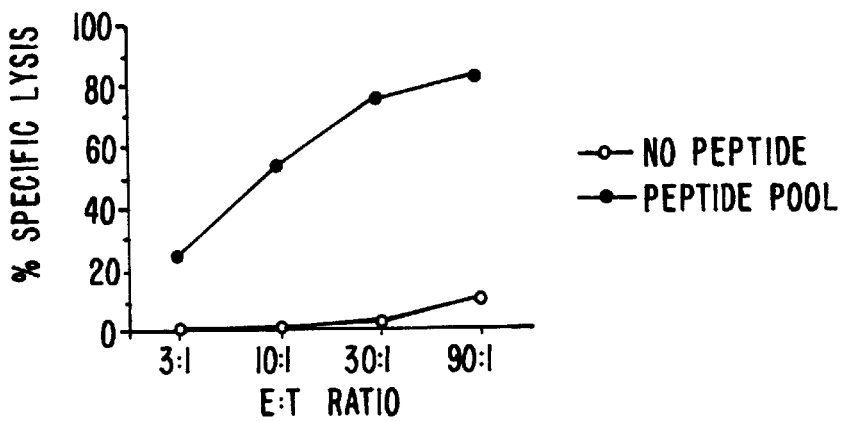
FIG. 7 (parts A–D) shows a comparison of different methods to load peptides onto SAC-I activated PBMCs as APCs. A pool of MAGE-3 HLA A1 binding peptides (1044.07:161–167 and 1044.01:8–17) were tested with donor GC 164. 7 A-acid strip; 7 B- cold temperature incubation; 7 C- room temperature, no preincubation or acid strip with 4 hour peptide loading only; 7 D- room temperature, no acid stripping with addition of soluble peptide to the culture.
Figure 7B:
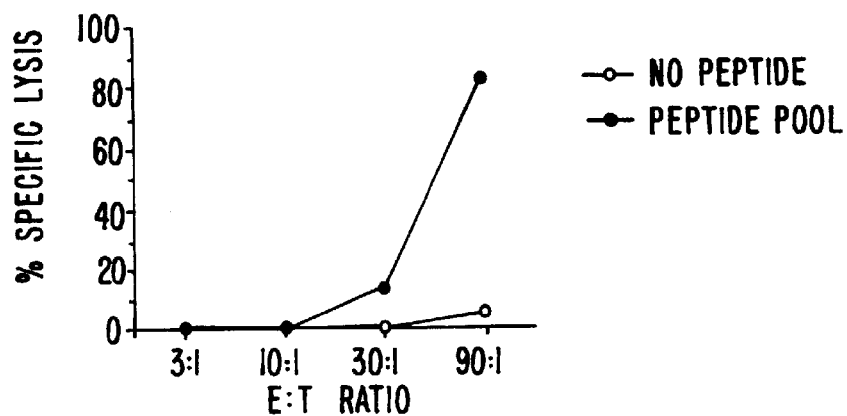
Figure 7C:
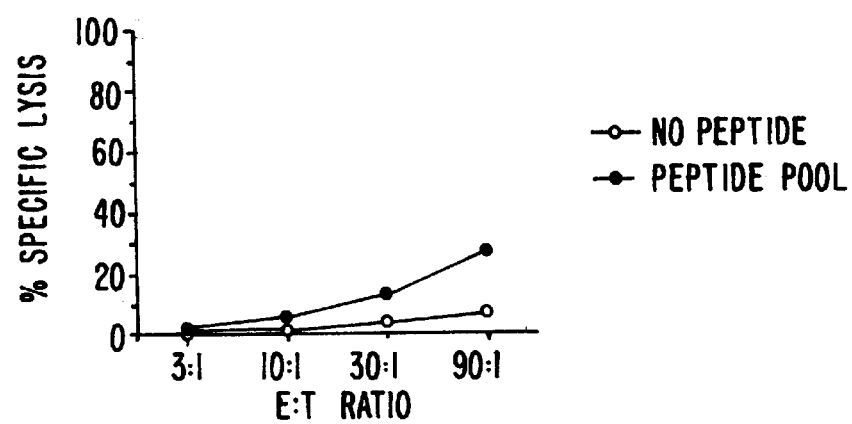
Figure 7D:
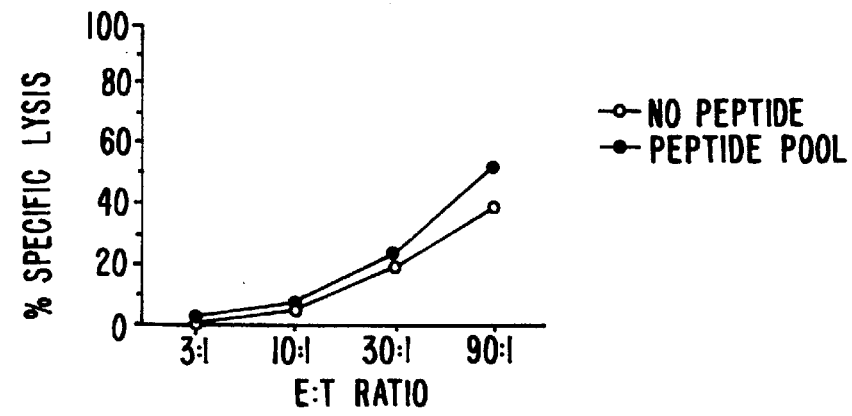

In Vitro Induction of Primary Antigen-Specific CTL Using Acid Stripped/Peptide Loaded APCS. Additional critical parameters for the induction of primary CTL are: 1) enrichment of CD8+ T-cells in the responder cell population (by depletion of CD4+ T-cells), 2) addition of rIL-7 to the CTL induction cultures from day 0, and 3) restimulation of the cultures with antigen on day 12–14 using autologous adherent cells pulsed with peptide. Results presented in FIGS. 2, 3 and 5 correspond to experiments performed using PBMC as APC. The results presented in FIG. 4 present results obtained using PHA-induced T-cell blasts as APC. FIG. 7 shows a comparison of the acid strip loading technique (FIG. 7a) to the cold temperature incubation technique (FIG. 7b).

EXAMPLE 3

Screening Peptides to Identify CTL Epitopes

In order to identify CTL epitopes, CTL were stimulated by SAC-I activated PBMCs as APC. Cold temperature enhanced expression of empty MHC enabling loading of antigenic peptide to generate SAC-I activated PBMC APC. This method presents an alternative protocol to the methods described above for the generation of the APC which are used to stimulate CTL. This example also presents an alternative protocol for the stimulation of CTL by the APC. Complete Culture Medium. The tissue culture medium used in this study consisted of RPMI 1640 with Hepes and L-glutamine (Gibco) (Biowhittaker) supplemented with 2 mM L-glutamine (Irvine Scientific), 0.5 mM sodium pyruvate (Gibco), 100 U/100 ug/ml penicillin/streptomycin (Irvine), and 5% heat-inactivated Human Serum Type AB (RPMI/5% HS; Gemini Bioproducts). Culture media used in the growth of EBV-transformed lines contained 10% heat-inactivated fetal calf serum (RPMI/10% FCS, Irvine) instead of human serum.

Cytokines. Recombinant human Interleukin-2 (rIL-2) and Interleukin-4 (rIL-4) were obtained from Sandoz and used at a final concentration of 10 U/ml and 10 ng/ml, respectively. Human interferon-γ (IFN-7) and recombinant human Interleukin-7 (rIL-7) were obtained from Genzyme and used at 20 U/ml and 10 ng/ml, respectively.

Peptides. Peptides were synthesized as described above and are described in Table 1. Peptides were routinely dissolved in 100% DMSO at 20 mg/ml, aliquoted, and stored at −70° C. until used.

Cell Lines. JY, Steinlein, EHM, BVR, and KT3 are homozygous human EBV-transformed cells B cell lines expressing HLA $A_{2.1}$, $A_1$, $A_3$, $A_{11}$, and $A_{24}$, respectively. They are grown in RPMI/10% FCS and used as targets in the CTL assays. K562, an NK cell sensitive, erythroblastoma line grown in RPMI/10% FCS, was used for reduction of background killing in the CTL assays. Melanoma HLA A1+ cell lines either expressing the MAGE antigen, mel 397 and mel 938 or those not expressing the MAGE antigen, mel 888, were also grown in RPMI/10% FCS.

Isolation of Peripheral Blood Mononuclear Cells (PBMCs). Whole blood was collected into heparin containing syringes and spun in 50 cc tubes at 1600 RPM (Beckman GS-6KR) for 15 minutes. The plasma layer was then removed and 10 ml of buffy coat was collected with a pipette using a circular motion. The buffy coat was mixed well and diluted with an equal volume of RPMI. The buffy coat (30 ml) was then layered on 20 ml of Ficoll-Paque (Pharmacia) and centrifuged at 1850 RPM (400×g) for 20 minutes, 25° C., with the brake off. The interface between the Ficoll and the plasma containing the PBMCs was recovered with a transfer pipet (two interfaces per 50 ml tube) and washed three times with 50 ml of RPMI (1700, 1500, and 1300 RPM for 10 minutes). Cells were resuspended in 10–20 ml of culture medium, counted, and adjusted to the appropriate concentration.

Freezing PBMCs. 30 million cells/tube (90% FCS/10% DMSO; Sigma) were inserted into a Nalgene Cryo 1° C. Freezing Container containing isopropanol (Fisher) and placed at −70° C. from 4 hrs (minimum) to overnight (maximum). The isopropanol was changed every five times. Tubes were transferred to liquid nitrogen for long term storage. To thaw, PBMCs were continuously shaken in a 37° C. water bath until the last crystal was almost thawed (tubes were not allowed to sit in the water bath or at room temperature for any period of time). Cells were diluted into serum-free RPMI containing 30 μg/ml DNase to prevent clumping by dead cell DNA and washed twice.

Induction of Primary CTL Using SAC-I Activated PBMCs as APCs a. Preparation of SAC-I activated PBMCs as APCS: PBMCs were purified using the standard Ficoll-Paque protocol and resuspended at $1\times10^6$/ml in RPMI/5% FCS containing 0.005% Pansorbin cells (SAC-I cells expressing Protein A; Calbiochem), 20 μg/ml Immunobeads (Rabbit anti-Human IgM; Biorad), and 20 ng/ml of human rIL-4. Two ml of cells per well were plated in a 24-well plate (Falcon, Becton Dickinson) and cultured at 37° C. After 3 days, the medium was removed and the cells were washed three times followed by addition of RPMI/10% HS. The cells were used after culturing for an additional 2 days in RPMI/10% HS.

b. Expression of empty Class I molecules on the surface of APCs and peptide loading of APCS.

1. Cold temperature incubation:

a. Expression of empty MHC in APCs: The APCs were adjusted to a concentration of $2 \times 10^6$/ml in complete culture medium containing 10 ng/ml rIL-4, 20 U/ml human IFN-γ, and 3 μg/ml β2-microglobulin ($β_2$m; Scripps Lab). The cells were then incubated overnight at 26° C. in the presence of 5% $CO_2$. It should be noted that these cells only express a fraction of Class I molecules in the empty state (~10%).

b. Peptide loading of APC stimulator cells: Empty Class I expressing APCs were washed 1–2 times with serum free RPMI (+L-glutamine and Hepes) and resuspended at $1 \times 10^7$ in serum-free RPMI containing 50 μg/ml total of the peptide pool (i.e., 16.7 μg/ml of each peptide in a pool of three; 25 μg/ml of each peptide in a pool of two; 50 μg/ml of individual peptide), 30 μg/ml DNAse, and 3 μg/ml $β_2$m. Following a 4 hour incubation at 20° C., the cells were irradiated at 6100 rads ($5 \times 10^6$/ml; 25 million cells/tube), washed and adjusted to the appropriate concentration for addition to the induction culture (see below).

2. Acid stripping: This was used as an alternative method for generating empty MHC on the surface of the APCs. The SAC-I activated PBMCs were washed once in cold 0.9% sodium chloride (J. T. Baker) containing 1% BSA. The cells were resuspended at $10^7$/ml in cold citrate-phosphate buffer (0.13M citric acid [J. T. Baker], 0.06M sodium phosphate monobasic [Sigma], pH3) containing 1% BSA and 3 μg/ml $β_2$m and incubated on ice. After 2 minutes, 5 volumes of cold 0.15M sodium phosphate buffer, pH7.5, containing 1% BSA, 3 μg/ml $β_2$m, and 10 μg/ml peptide [neutralizing buffer #1] was added and the cells centrifuged at 1500 RPM for 5 minutes at 4° C. The cells were resuspended in 1 ml of cold PBS containing 1% BSA, 30 μg/ml DNase, 3 μg/ml $β_2$microglobulin, and 50 μg/ml peptide [neutralizing buffer #2] and incubated for 4 hours at 20° C. As above, subsequent to the four hour incubation at 20° C., the cells were irradiated at 6100 rads ($5 \times 10^6$/ml; 25 million cells/tube), washed, then adjusted to the appropriate concentration for addition to the induction culture (see below).

c. Preparation of the CD4+ depleted PBMC responder cell population (depletion of lymphocyte subpopulations using AIS flasks). AIS MicroCellector T-150 flasks (specific for the depletion of CD4+ T cells; Menlo Park, Calif.) were primed by adding 25 ml of PBS/1 mM EDTA, swirling for 30 seconds so that all surfaces were moistened, and then incubating with the binding surface down at room temperature for 1 hour. Following this incubation, flasks were shaken vigorously for 30 seconds, washed 1 time with PBS/EDTA, 2 additional times with PBS and then incubated with 25 ml of culture medium for 15 minutes. PBMCs were thawed in serum-free RPMI (+L-glutamine+Hepes) containing 30 μg/ml DNAse, washed once, and incubated for 15 minutes in culture medium. Following aspiration of culture medium from the flasks, up to 180 million PBMCs were added in 25 ml of culture medium containing 30 μg/ml DNAse. After 1 hour at room temperature, the flasks were rocked gently for 10 seconds to resuspend the nonadherent cells. The nonadherent cell suspension containing the CD8+ T cells was collected and the flasks were washed 2 times with PBS. The CD4+ T cell depleted PBMCs were centrifuged and counted for addition to the induction culture. The CD4+ and CD8+ phenotype of the CD4+ depleted cell population was determined by FACS analysis (see below). In general, this technique resulted in a two-fold enrichment for CD8+ T cells with an average of approximately 40–50% CD8+ T cells and 15–20% remaining CD4+ T cells following depletion of CD4+ T cells. Depletion of CD4+ T cells can also be accomplished by using antibody and complement methods or antibody coated magnetic beads (Dynabeads). Depletion of CD4+ T cells enriched the CTLP and removed cells which competed for cell nutrients.

d. Induction of primary CTL. During the 4 hour peptide loading of the stimulator APCs, CD4+ depleted PBMC to be used as the responder population were prepared utilizing AIS flasks for selection of CD8+ T cells through the depletion of CD4+ T cells (above). The responder cells were plated at $3 \times 10^6$/ml in a 1 ml volume (24 well plate) and placed at 37° C. until the peptide loaded stimulator APCs were prepared. The irradiated, peptide loaded APCs were washed 1 time in serum-free RPMI (+L-glutamine and Hepes), adjusted to the appropriate concentration in complete medium, and plated into a 24 well plate at 1 ml/plate: For PBMC and SAC-I activated PBMCs as APCs $1 \times 10^6$ stimulator cells (1 ml volume) were plated into the wells containing the responder cells; For PHA blasts as APCs, 1 ml of $3 \times 10^5$/ml stimulator cells were plated in each well. A final concentration of 10 ng/ml of rIL-7 (2 ml total volume) was added. On day 7 an additional 10 μg/ml rIL-7 was added to the culture and 10 U/ml rIL-2 was added every 3 days thereafter. On day 12, the cultures were restimulated with peptide pulsed adherent cells and tested for cytolytic activity 7 days later (below).

Protocol for Restimulation of Primary CTL Using Autologous Adherent APC. Autologous PBMCs were thawed into serum-free RPMI (+L-glutamine and Hepes) containing 30 g/ml DNAse, washed 2 times, and adjusted to $5 \times 10^6$/ml in culture medium containing DNAse. PBMCs (25 million cells/tube in 5 ml) were irradiated at 6100R. After 1 wash, the PBMCs were resuspended in culture medium and adjusted to $4 \times 10^6$/ml and 1 ml of irradiated PBMCs was added per well of a 24-well plate. The PBMC were incubated for 2 hours at 37° C., washed 3 times to remove nonadherent cells, and cultured in medium containing 20 μg/ml total peptide and 3 μg/ml $β_2$microglobulin added in a 0.5 ml volume and again incubated for 2 hours at 37° C. The peptide was aspirated and $1.5 \times 10^6$ responder cells resuspended in culture medium were added in a 1 ml volume. After 2 days, 1 ml of culture medium containing 20 U/ml rIL-2 was added.

FACS Analysis. One million cells/tube were centrifuged, resuspended in 100 μl/tube PBS/0.1% BSA/0.02% sodium azide (Sigma) plus 10 μl/tube directly conjugated antibody (Becton Dickinson), and incubated on ice 15–20 minutes. Cells were then washed 2 times with PBS/0.1% BSA/0.02% sodium azide and resuspended in PBS to analyze on FACScan (Becton Dickinson). When it was not possible to analyze samples within 1–2 days, cells were fixed with PBS containing 1% paraformaldehyde (Fisher) and analyzed within one week.

Figure 6:
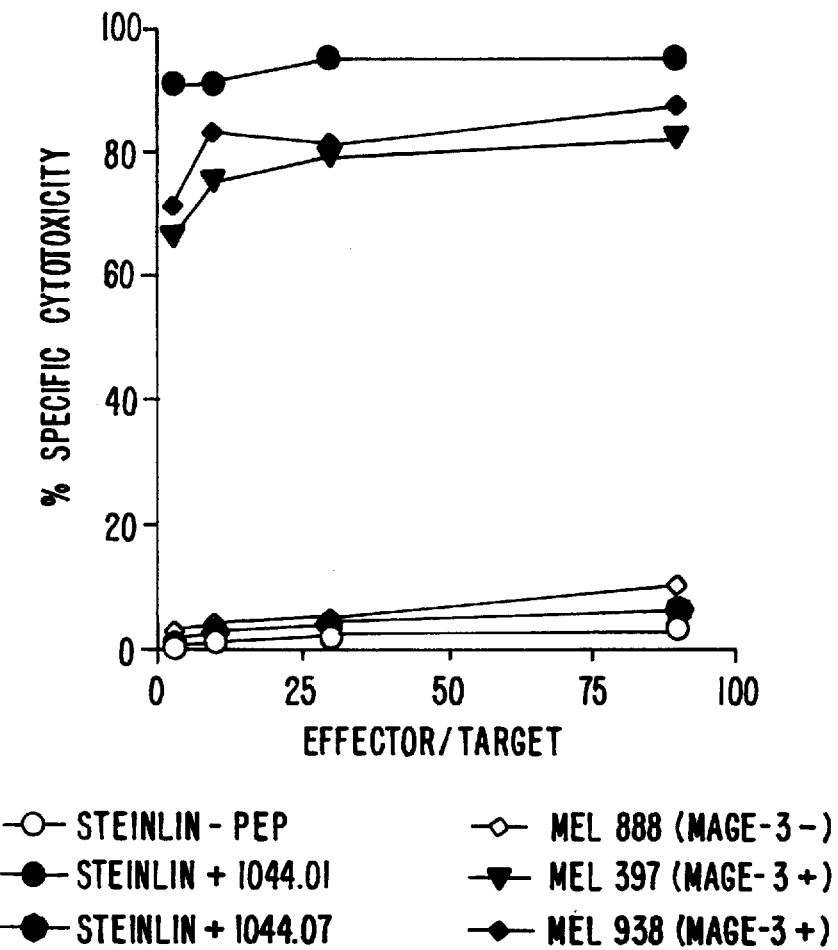
FIG. 6 shows CTL induction using GC 30, HLA A1 responders and autologous cold temperature incubated SAC-I activated PBMC$_8$ as stimulators after loading with 1044.07 MAGE-3 (161–169) peptides.
Figure 8A:
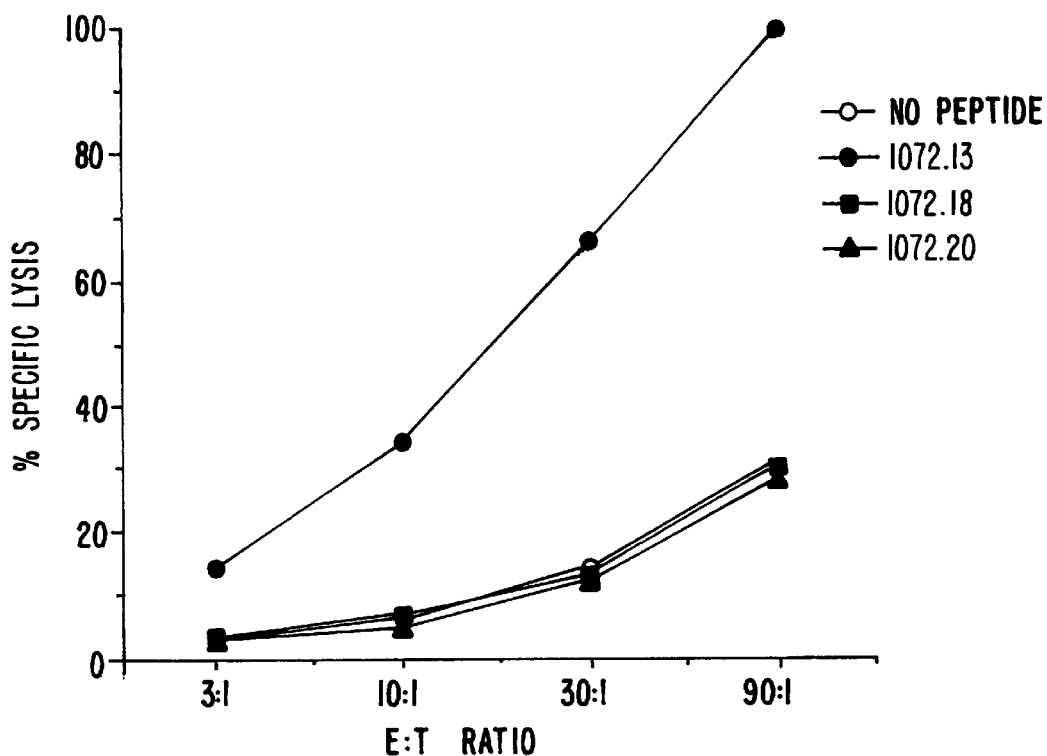
FIG. 8 shows the result of the CTL induction assay using selected MAGE peptides.
Figure 8B:
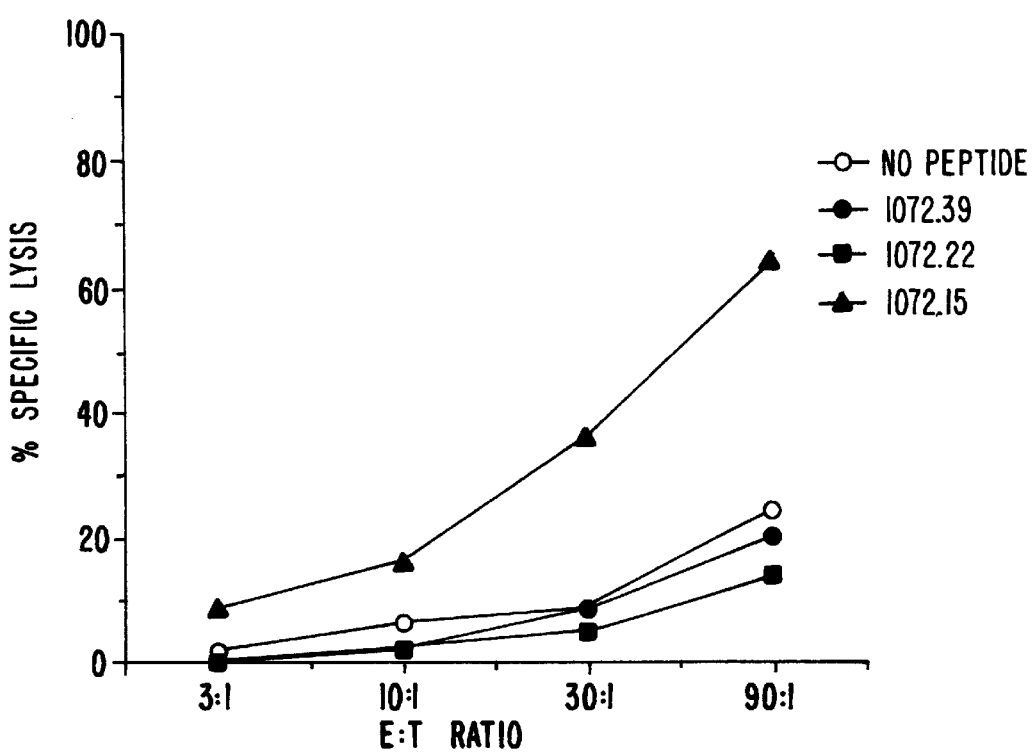
Figure 9A:
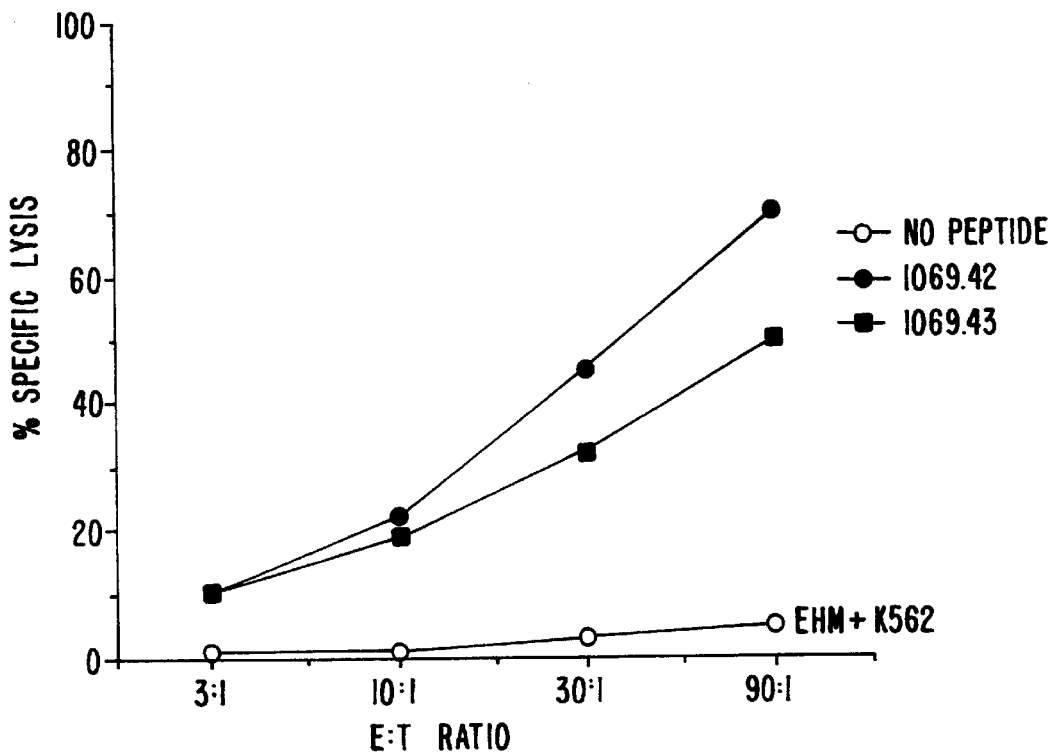
FIG. 9 shows the result of the CTL induction assay using selected HIV peptides.
Figure 9B:
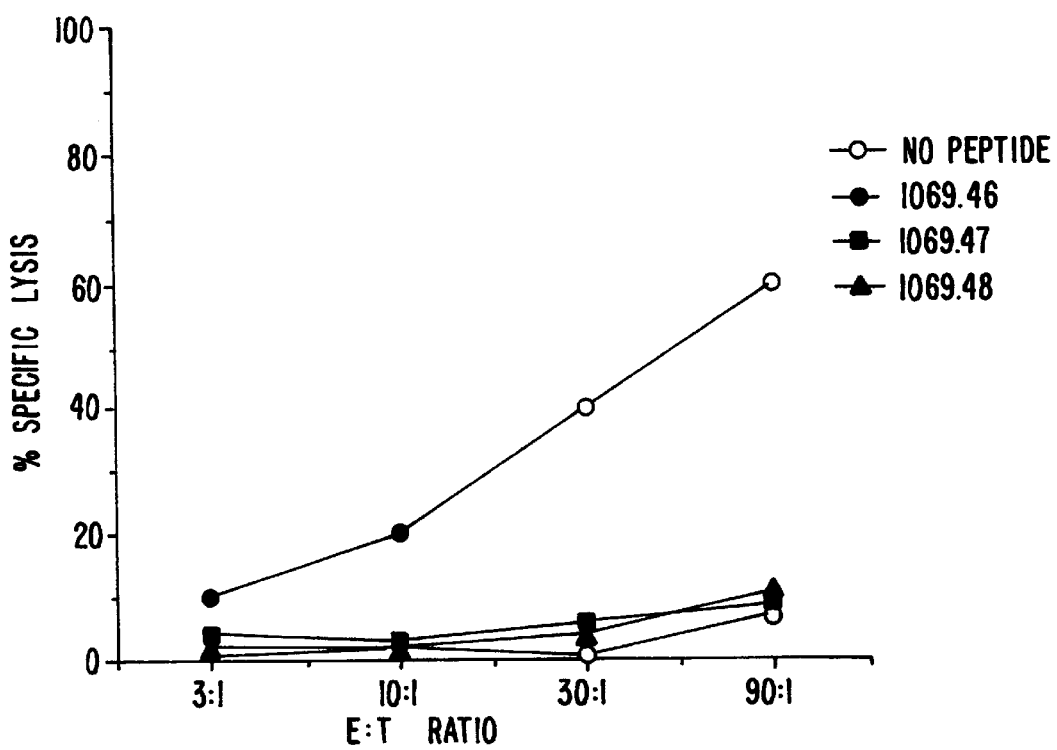
Figure 10:
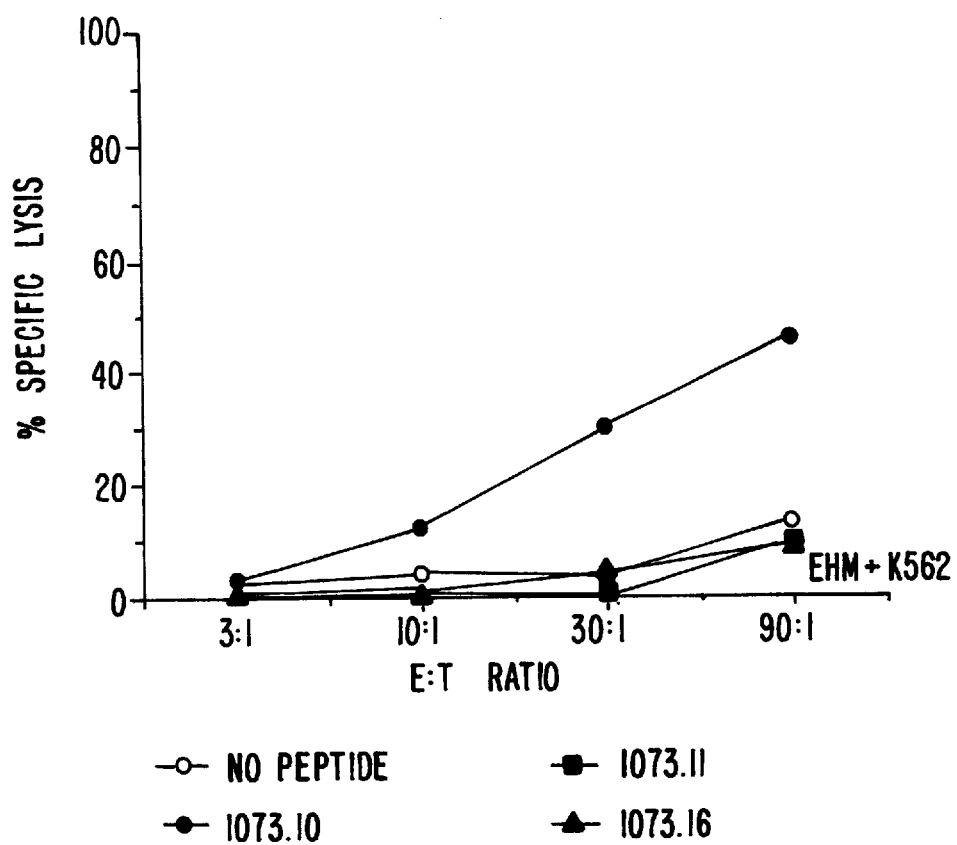
FIG. 10 shows the result of the CTL induction assay using selected HCV peptides.
Figure 11:
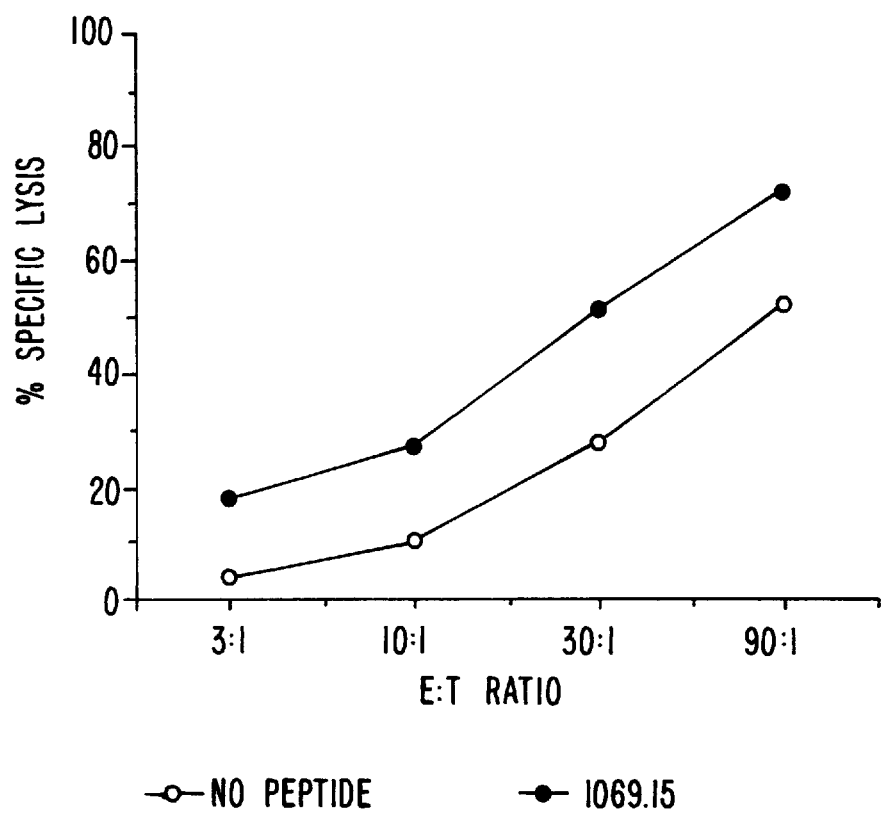
FIG. 11 shows the retuls of the CTL induction assay using selected HBV peptides.

Cytotoxicity Assay a. Target cell Preparation. Approximately 16–20 hours prior to the CTL assay, target cells (Class I matched EBV-transformed lines) were washed once and resuspended in a 10 ml volume at $3 \times 10^5$/ml in RPMI/5% FCS in the presence or absence of 10 μg/ml total peptide.

b. Labeling of target cells: Target cells were centrifuged and resuspended in 200 μl/tube sodium $^{51}$Cr chromate (NEN), then incubated at 37° C. for 1 hour on a shaker. Targets were washed 3 times (10 ml/wash) with RPMI/10% FCS and resuspended in 10 ml (to determine the efficiency of labelling, 50 μl/target was counted on the Micromedic automatic gamma counter).

c. CTL assay. Target cells were adjusted to 2×10⁵/ml and 50 µl of the cell culture was added to each well of a U-bottomed 96-well plate (Costar Corp.) for a final concentration of 1×10⁴/well. K562 cells were washed once, resuspended at 4×10⁶/ml, and 50 µl/well was added for a final concentration of 2×10⁵/well (ratio of cold K562 to target was 20:1). Responder cells were washed once, resuspended at 9×10⁶/ml, and three fold serial dilutions were performed for effector to target ratios of 90:1, 30:1, 10:1, and 3:1. Responder cells were added in a volume of 100 µl in duplicate wells. For spontaneous release, 50 Al/well of labelled target cells, 50 µl/well K562, and 100, µl/well of medium was added. For maximum release, 50 µl/well target, 50 µl/well K562, and 100 µl/well of 0.1% Triton-X100 (Sigma) was added. Plates were centrifuged for 5 minutes at 1200 RPM. Following a 5 hour incubation at 37° C., plates were centrifuged again for 5 minutes at 1200 RPM, and 100 µl/well of supernatant was collected. Standard gamma counting techniques (Micromedic automatic gamma counter; 0.5 minutes/tube) were used to determine the percent specific lysis according to the formula: % specific lysis=cpm experimental release—cpm spontaneous release/cpm maximum release—cpm spontaneous release ×100. A cytotoxicity assay (CTL assay) was considered positive if the lysis by CTL of targets sensitized with a specific peptide at the two highest effector to target (E:T) ratios was 15% greater than lysis of control targets (i.e. target cells without peptide). A cytotoxicity assay (CTL assay) was considered borderline if the lysis by CTL of targets sensitized with a specific peptide at the two highest effector to target (E:T) ratios was 6% greater than lysis of control targets (i.e. target cells without peptide).

d. Results of the peptides that bind to the indicated alleles, 12 of the 60 MAGE peptides, 13 of the 53 HIV peptides, 3 of the 25 HCV peptides, and 7 of the 28 HBV peptides tested to date induced primary CTL in vitro. Representative graphs illustrating CTL responses to various immunogenic peptides are shown for MAGE (FIG. 8), HIV (FIG. 9), HCV (FIG. 10), and HBV (FIG. 11). The CTL induction data is summarized in Table 3 which lists the immunogenic peptides which bind to the appropriate MHC and induce primary CTL in vitro. Indicated is the peptide's sequence, corresponding antigen and HLA allele to which it binds. Results shown in FIG. 6 illustrate lysis of peptide sensitized targets and endogenous targets following stimulation with SACI activated PBMCs loaded with the immunogenic peptide MAGE-3 1044.07 which had been loaded using cold temperature incubation.

Although the present invention has been described in some detail by way of illustration and example for purposes of clarity and understanding, it will be apparent that certain changes and modifications may be practiced within the scope of the appended claims.

TABLE 1

Peptides Synthesized For Loading Onto Acid Stripped Autologous PBMCs and PHA Blasts

| Peptide ID # | Antigen | Sequence |
|---|---|---|
| 777.03 | HBVs 20–28 | FLLTRILTI |
| 924.07 | HBVc 18–27 | FLPSDFFPSV |
| 927.32 | HBVp 61–69 | GLYSSTVPV |
| 938.01 | MAGE 1 161–169 | EADPTGHSY |
| 939.03 | PSA 49–57 | VLVHPQWVL |
| 941.01 | HBVc 18–27 analog | FLPSDYFPSV |
| 1044.04 | PAP 135–143 | ILLWDPIPV |

TABLE 1-continued

Peptides Synthesized For Loading Onto Acid Stripped Autologous PBMCs and PHA Blasts

| Peptide ID # | Antigen | Sequence |
|---|---|---|
| 1044.05 | PSA 166–175 | KLQCVDLVHI |
| 1044.06 | PSA 118–128 | MLLRLSEPAEL |
| 1044.07 | MAGE 3 161–169 | EVDPIGHLY |
| 1044.01 | MAGE 3 8–17 | ASSLPTTMNY |
| 1072.13 | MAGE 1 96–104 | SLFRAVITK |
| 1072.18 | MAGE 1 66–74 | TTINFTRQR |
| 1072.20 | MAGE 1 219–227 | SVMEVYDGR |
| 1072.39 | MAGE 1N 270–279 | RALAETSYVK |
| 1072.22 | MAGE 1 238–247 | LLTQDLVQEK |
| 1072.15 | MAGE 1 95–104 | ESLFRAVITK |
| 1069.42 | HIV pol 1225–1235 | KVYLAWVPAHK |
| 1069.43 | HIV env 2185–2194 | TVYYGVPVWK |
| 1069.46 | HIV pol 1032–1042 | WTYQIYQEPFK |
| 1069.47 | HIV env 2184–2194 | VTVYYGVPVWK |
| 1069.48 | HIV pol 1434–1443 | AVFIHNFKRK |
| 1073.10 | HCV LORF 1858–1867 | GVAGALVAFK |
| 1073.11 | HCV CORE 43–51 | RLGVRATRK |
| 1073.16 | HCV LORF 1227–1236 | HLHAPTGSGK |
| 1069.15 | HBV pol 724–733 | TLWKAGILYK |

TABLE 2

Acid Stripping, Peptide Loading of JY Cells with Radiolabelled 941.01

| Cell Population | ¹²⁵I-Labeled Peptide +/– Cold Peptide | CPMS +/– std. dev. | |
|---|---|---|---|
| JY acid stripped | – cold peptide | 3553 ± 157 | n = 3 |
| JY acid stripped | + cold peptide | 13 | n = 1 |
| JY control | – cold peptide | 370 ± 37 | n = 3 |
| JY control | + cold peptide | 50 | n = 1 |

TABLE 3

| Sequence | Antigen | Motif | Id |
|---|---|---|---|
| EVDPIGHLY | MAGE3 | A01 | 1044.07 |
| ASSLPTTMNY | MAGE3 | A01 | 1044.01 |
| EADPTGHSY | MAGE1 | A01 | 958.01 |
| SSLPTTMNY* | MAGE3 | A01 | 1072.02* |
| GSVVGNWQY* | MAGE3 | A01 | 1072.03* |
| ALAETSYVK* | MAGE1N | A03 | 1072.38* |
| SLFRAVITK | MAGE1 | A11 | 1072.13 |
| RALAETSYVK | MAGE1N | A11 | 1072.39 |
| ESLFRAVITK | MAGE1 | A11 | 1072.15 |
| KVYLAWVPAHK | HIV | A3/11* | 1069.42* |
| TVYYGVPWK | HIV | A03 | 1069.43 |
| KLACRWPVK | HIV | A03 | 1069.44 |
| KMIGGIGGFIK | HIV | A03 | 1069.45 |
| AIFQSSMTK | HIV | A03 | 966.01 |
| WTYOQIYQEPFK | HIV | A03 | 1069.46 |
| FLGKIWPSHK* | HIV | A03 | 1069.56* |
| TVYYGVPVWK | HIV | A11 | 1052.03 |
| VTVYYGVPVWK | HIV | A11 | 1069.47 |
| GVAGALVAFK | HCV | A03 | 1073.10 |
| CTCGSSDLY | HCV | A11 | 1069.62 |
| GVAGALVAFK | HCV | A11 | 1052.05 |
| LLDTASALY* | HBV | A01 | 1069.01* |
| TLWKAGILYK | HBV | A03 | 1069.15 |

*borderline positive

What is claimed is:

1. A method for activating cytotoxic T cells in vitro comprising:

dissociating bound peptides from class I MHC molecules on antigen presenting cells, using a mild acid treatment;

associating desired immunogenic peptides with the class I MHC molecules on the antigen presenting cells; and incubating the antigen presenting cells with the cytotoxic T cells in the presence of a growth factor, thereby producing activated cytotoxic T cells.

2. The method of claim 1, wherein the step of dissociating bound peptides is carried out by incubating the antigen presenting cells in a glycine or citrate-phosphate buffer solution at pH 3.

3. The method of claim 1, wherein the step of associating desired immunogenic peptides with the MHC molecules is carried out by incubating the antigen presenting cells with about 10 to 50 µg/ml immunogenic peptide.

4. The method of claim 1, wherein the step of incubating the antigen presenting cells with the cytotoxic T cells occurs over a period of about 7 to 10 days.

5. The method of claim 1 wherein the antigen presenting cells are peripheral blood mononuclear cells isolated from a patient.

6. The method of claim 5 wherein the peripheral blood mononuclear cells are SAC-I activated.

7. The method of claim 1 wherein the growth factor is IL-7 and said growth factor is added at the start of the incubation step and at 7 days after beginning the incubation step.

8. The method of claim 1 wherein the growth factor is IL-2 and said growth factor is added 7 days after the beginning of the incubation step.

9. The method of claim 1, further comprising: contacting the activated cytotoxic T cells with an acceptable carrier, thereby forming a pharmaceutical composition; and administering the pharmaceutical composition to a patient.

10. The method of claim 9, further comprising separating the activated cytotoxic T cells from the antigen presenting cells before contacting the activated cytotoxic T cells with an acceptable carrier.

11. The method of claim 9 wherein the cytotoxic T cells are useful in the treatment of cancer, AIDS, hepatitis, bacterial infection, fungal infection, malaria or tuberculosis.

12. A method of specifically killing target cells in a human patient, comprising:

obtaining a fluid sample containing cytotoxic T cells from the patient;

contacting the cytotoxic T cells with antigen presenting cells, wherein said antigen presenting cells are produced by the steps of:
(a) dissociating bound peptides from the class I MHC molecules on said antigen presenting cells using a mild acid treatment; and
(b) associating desired immunogenic peptides with said class I MHC molecules on said antigen presenting cells;

thereby producing activated cytotoxic T cells;

contacting the activated cytotoxic T cells with an acceptable carrier, thereby forming a pharmaceutical composition; and administering the pharmaceutical composition to a patient.

13. The method of claim 12, further comprising the step of dissociating bound peptides from the antigen presenting cells by incubating the antigen presenting cells in a glycine or citrate-phosphate buffer solution at pH 3.

14. The method of claim 12, further comprising the step of associating desired immunogenic peptides with the MHC molecules on the antigen presenting cells by incubating the antigen presenting cells with about 10 to about 50 µg/ml immunogenic peptide.

15. The method of claim 12, wherein the antigen presenting cells are peripheral blood mononuclear cells isolated from a patient.

16. The method of claim 12, wherein the step of incubating the cytotoxic T cells with the antigen presenting cells occurs over a period of about 7 to 10 days.

* * * * *